United States Patent
Matsukura et al.

(10) Patent No.: US 10,024,813 B2
(45) Date of Patent: Jul. 17, 2018

(54) GAS DETECTION APPARATUS

(71) Applicant: NGK SPARK PLUG CO., LTD., Nagoya-shi, Aichi (JP)

(72) Inventors: Yusuke Matsukura, Nagoya (JP); Shoji Kitanoya, Kasugai (JP); Masaya Watanabe, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 439 days.

(21) Appl. No.: 14/811,206

(22) Filed: Jul. 28, 2015

(65) Prior Publication Data

US 2016/0033436 A1 Feb. 4, 2016

(30) Foreign Application Priority Data

Jul. 31, 2014 (JP) .................................. 2014-156628

(51) Int. Cl.
*G01N 27/12* (2006.01)
(52) U.S. Cl.
CPC ......... *G01N 27/121* (2013.01); *G01N 27/124* (2013.01)
(58) Field of Classification Search
CPC ........................... G01N 27/121; G01N 27/124
USPC ....................................................... 73/29.02
See application file for complete search history.

(56) References Cited

U.S. PATENT DOCUMENTS

| | | | | |
|---|---|---|---|---|
| 5,189,902 A | * | 3/1993 | Groeninger | G01N 29/036 73/24.06 |
| 9,494,319 B2 | * | 11/2016 | Sutton | F23K 1/00 |
| 2005/0030172 A1 | | 2/2005 | Right et al. | |
| 2012/0111978 A1 | * | 5/2012 | Murphy | B02C 15/04 241/25 |
| 2012/0237402 A1 | * | 9/2012 | Cantarelli | F02D 41/1448 422/111 |
| 2014/0020448 A1 | | 1/2014 | Matsukura et al. | |

FOREIGN PATENT DOCUMENTS

| | | |
|---|---|---|
| JP | 11-241820 A | 9/1999 |
| JP | 2005-52833 A | 3/2005 |
| JP | 2006-10670 A | 1/2006 |
| JP | 4302611 B2 | 7/2009 |
| JP | 2014-20859 A | 2/2014 |

OTHER PUBLICATIONS

Communication dated Dec. 26, 2017 from the Japanese Patent Office in counterpart application No. 2014-156628.

\* cited by examiner

*Primary Examiner* — Daniel S Larkin
(74) *Attorney, Agent, or Firm* — Sughrue Mion, PLLC

(57) ABSTRACT

A gas detection apparatus (1) which includes a gas detection element (3) including a heat generation resistor (34); an energization control section (7) which switches the energization state of the heat generation resistor to alternately assume one of two resistance values corresponding to one of two set temperatures set in advance; and a casing member (90) which accommodates the gas detection element and has a gas inlet opening (92h). The gas detection apparatus further includes a humidity computation section (7) which computes the humidity of the object atmosphere based on a ratio of a high-temperature-time voltage VH to a low-temperature-time voltage VL; and a clogging determination section (7) which determines the degree of clogging of the gas inlet opening based on a change in the humidity computed by the humidity computation section.

4 Claims, 14 Drawing Sheets

GAS DETECTION APPARATUS

BACKGROUND OF THE INVENTION

1. Field of the Invention

The present invention relates to a gas detection apparatus which detects the concentration of a gas present in an object atmosphere.

2. Description of the Related Art

In recent years, in order to satisfy social needs such as protection of the environment and nature, research has actively been conducted on fuel cells which are efficient and clean energy sources. Among them, polymer electrolyte fuel cells (PEFC) and hydrogen internal combustion engines are expected as energy sources for homes, vehicles, etc., because they can operate at low temperature and have a high output density.

In these systems, detection of gas leakage is important because these systems use hydrogen, which is a combustible gas, as fuel.

A combustible gas detection apparatus has been known which detects the concentration of such a combustible gas present in an object atmosphere. The known combustible gas detection apparatus includes a gas detection element which is disposed in an object atmosphere and which includes a heat generation resistor and a temperature measurement resistor provided thereon. The resistance of the heat generation resistor changes due to a change in the temperature of the heat generation resistor itself (due to heat generation of the heat generation resistor). The resistance of the temperature measurement resistor changes due to a change in environmental temperature.

Specifically, in this combustible gas detection apparatus, the resistance of the heat generation resistor in the gas detection element is controlled using a bridge circuit such that the resistance alternately becomes equal to resistance values corresponding to two set temperatures (first and second set temperatures). Further, the concentration of combustible gas is calculated from control voltages (voltages across the heat generation resistor) at that time and a voltage difference (temperature voltage) produced as a result of a change in the resistance of the temperature measurement resistor.

The switching between the two set temperatures (first and second set temperatures) is performed, for example, by alternately selecting fixed resistors which are provided in the bridge circuit and have different resistance values every time a predetermined period of time has elapsed (see, for example, Patent Documents 1 and 2). As a result, by using one bridge circuit and a heat generation resistor, the voltages across the heat generation resistor at the first and second set temperatures can be detected, whereby the size of the gas detection element can be decreased, and power consumption can be suppressed.

Also, according to Patent Documents 1 and 2, considering that the concentration of combustible gas contained in an object atmosphere changes with the humidity of the object atmosphere, not only the above-described voltage difference, but also the ratio (voltage ratio) of the voltage generated across the heat generation resistor at the first set temperature to the voltage generated across the heat generation resistor at the second set temperature is computed. Further, the gas concentration is corrected by making use of the fact that this ratio is approximately proportional to the humidity.

Meanwhile, in the above-described combustible gas detection apparatus, the gas detection element is accommodated in a casing member having a gas inlet opening. Further, the object atmosphere is allowed to flow into the casing member and flow out of the casing member through the gas inlet opening, whereby detection by the gas detection element is enabled. However, if dirt, water, oil, or the like adheres to the gas inlet opening and the gas inlet opening is clogged (clogging), detection of the gas becomes inaccurate or impossible. Therefore, a determination as to whether or not the gas inlet opening is clogged must be made.

In view of the above, a technique has been developed for determining whether or not the gas inlet opening is clogged (see Patent Document 3). According to this technique, a monitor (air flow monitor) which measures the flow of air is disposed within the casing member, and a determination as to whether or not the gas inlet opening is clogged is made based on a change in the flow rate of air.

[Patent Document 1] Japanese Patent No. 4302611
[Patent Document 2] Japanese Patent Application Laid-Open (kokai) No. 2014-20859
[Patent Document 3] Japanese Patent Application Laid-Open (kokai) No. 2005-52833

Problems to be Solved by the Invention

However, in the case of the technique described in Patent Document 3, an air flow monitor must be additionally disposed in the combustible gas detection apparatus, which results in an increase in the number of components. Therefore, the above conventional technique is disadvantageous in that the product cost increases and it becomes difficult to make the gas detection apparatus compact.

SUMMARY OF THE INVENTION

It is therefore an object of the present invention to provide a gas detection apparatus which can readily determine the degree of clogging of a gas inlet opening of a casing member of the gas detection apparatus without increasing the number of device components.

The above object of the invention has been achieved by providing (1), a gas detection apparatus comprising a gas detection element which is disposed in an object atmosphere and includes a heat generation resistor whose resistance changes with a change in temperature of the heat generation resistor itself; an energization control section which switches the energization state of the heat generation resistor when a predetermined period of time has elapsed such that the heat generation resistor alternately assumes one of two resistance values corresponding to one of two set temperatures set in advance; and a casing member which accommodates the gas detection element and has a gas inlet opening through which the object atmosphere flows between a space inside the casing member and a space outside the casing member. The gas detection apparatus further comprises a humidity computation section which computes the humidity of the object atmosphere based on the ratio of a high-temperature-time voltage to a low-temperature-time voltage, the high-temperature-time voltage being a voltage developed across the heat generation resistor and detected at the high-temperature-side set temperature of the two set temperatures, and the low-temperature-time voltage being a voltage developed across the heat generation resistor and detected at the lower-temperature-side set temperature of the two set temperatures; and a clogging determination section which determines the degree of clogging of the gas inlet opening based on a change in the humidity computed by the humidity computation section.

According to the above gas detection apparatus (1), the humidity of the object atmosphere is calculated from the high-temperature-time voltage and the low-temperature-time voltage measured by the gas detection element, and the degree of clogging of the gas inlet opening is determined based on a change in humidity with time. Therefore, it is unnecessary to dispose an additional member for measuring the degree of clogging, such as an air flow monitor, in the gas detection apparatus. Therefore, the degree of clogging of the gas inlet opening can be readily determined without increasing the number of components.

In a preferred embodiment (2) of the above gas detection apparatus (1), the clogging determination section determines that the gas inlet opening is clogged in the case where a change in the humidity with time exceeds a first threshold within a predetermined period of time after the gas detection apparatus has been started.

According to the above gas detection apparatus (2), the degree of clogging of the gas inlet opening can be determined reliably by detecting a phenomenon whereby the humidity increases with time when the gas inlet opening is clogged. This is because the temperature within the apparatus rises within a short period of time after the gas detection apparatus has been started.

In another preferred embodiment (3) of the gas detection apparatus (1) or (2) above, the clogging determination section determines that the gas inlet opening is clogged in the case where a predetermined time has elapsed after the gas detection apparatus has been started and a change in the humidity with time does not exceed a second threshold.

According to the above gas detection apparatus (3), the degree of clogging of the gas inlet opening can be determined reliably by detecting the occurrence of a phenomenon whereby a change in the humidity is suppressed when the gas inlet opening is clogged. This is because the temperature within the apparatus becomes substantially constant after elapse of a time after startup of the gas detection apparatus.

Effect of the Invention

According to the present invention, it is possible to readily determine the degree of clogging of the gas inlet opening of the casing member of the gas detection apparatus without increasing the number of device components.

BRIEF DESCRIPTION OF THE DRAWINGS

FIGS. 5($a$) and 5($b$) represent time charts showing timings at which VH and VL are obtained, FIG. 5($c$) represents a time chart showing a first set temperature (CH) and a second set temperature (CL) of a heat generation resistor, and FIG. 5($d$) represents a time chart showing timings at which the temperature of a temperature measurement resistor is obtained.

DESCRIPTION OF REFERENCE NUMERALS AND SYMBOLS

Figure 1:
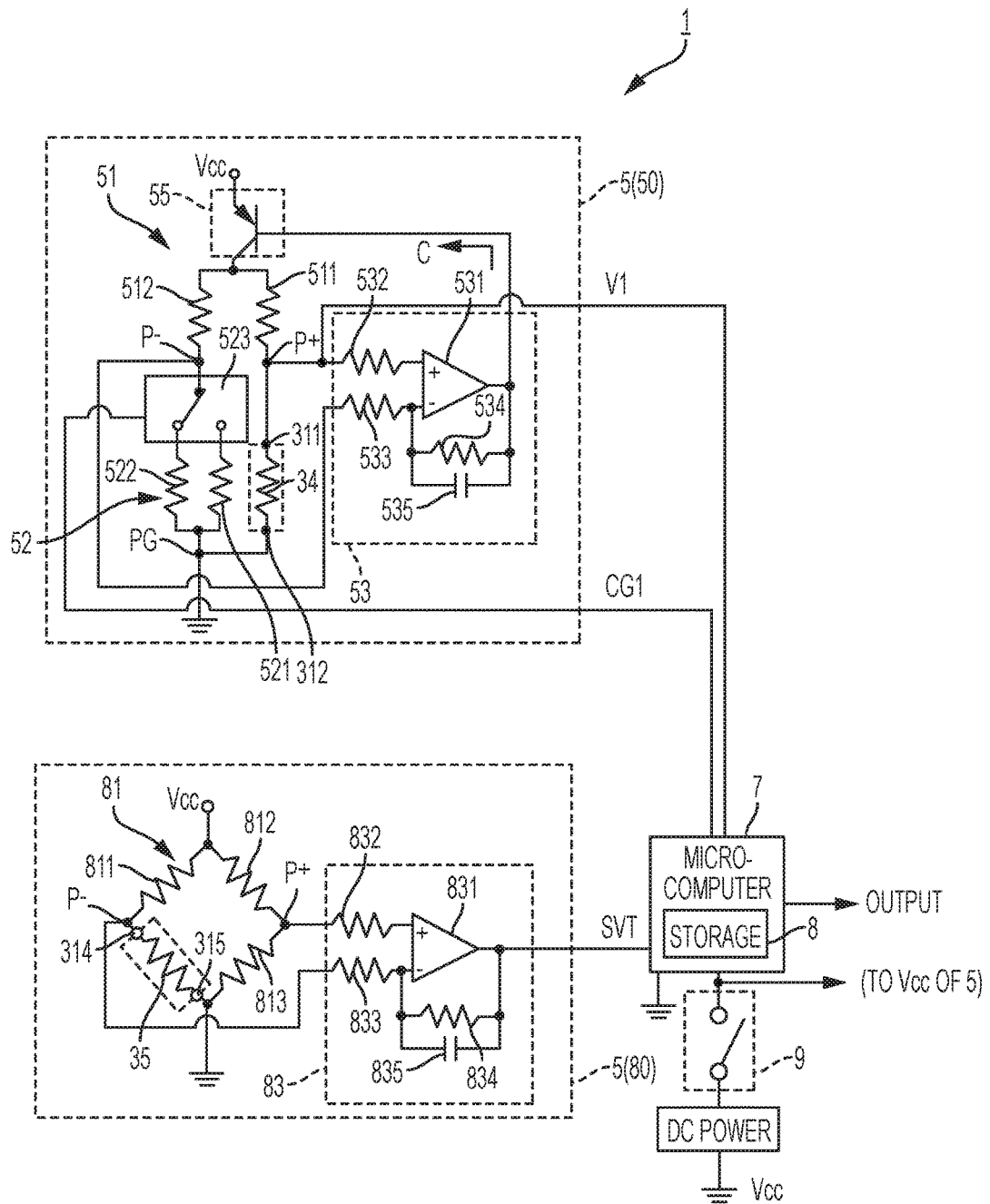
FIG. 1 is a diagram showing the overall configuration of a combustible gas detection apparatus.

Reference numerals used to identify various features in the drawings include the following.

1: gas detection apparatus
3: gas detection element
7: microcomputer (energization control section, gas concentration computation section, humidity computation section, clogging determination section)
34: heat generation resistor
35: temperature measurement resistor
50: energization control circuit (energization control section)
90: casing member
92$h$: gas inlet opening
CH: first set temperature
CL: second set temperature
VH: high-temperature-time voltage
VL: low-temperature-time voltage
TW: time period
T: environmental temperature

DETAILED DESCRIPTION OF THE PREFERRED EMBODIMENTS

The present invention will now be described in greater detail with reference to the drawings. However, the present invention should not be construed as being limited thereto.

Figure 2:
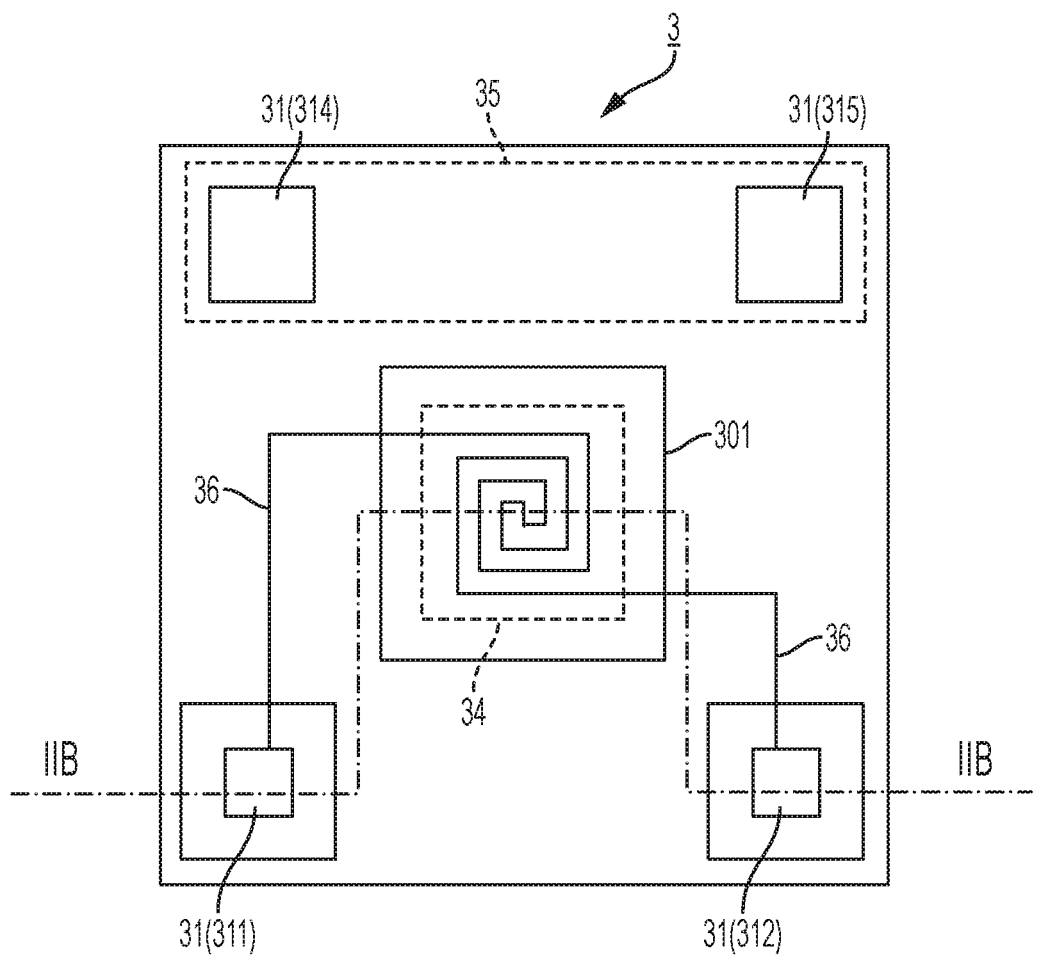
FIG. 2 is a plan view showing the structure of a gas detection element which is a main portion of the combustible gas detection apparatus.
Figure 3:
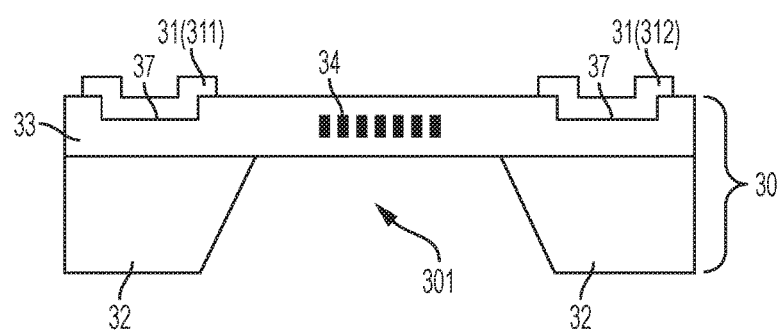
FIG. 3 is a cross-sectional view of the gas detection element taken along line IIB-IIB in FIG. 2.
Figure 4:
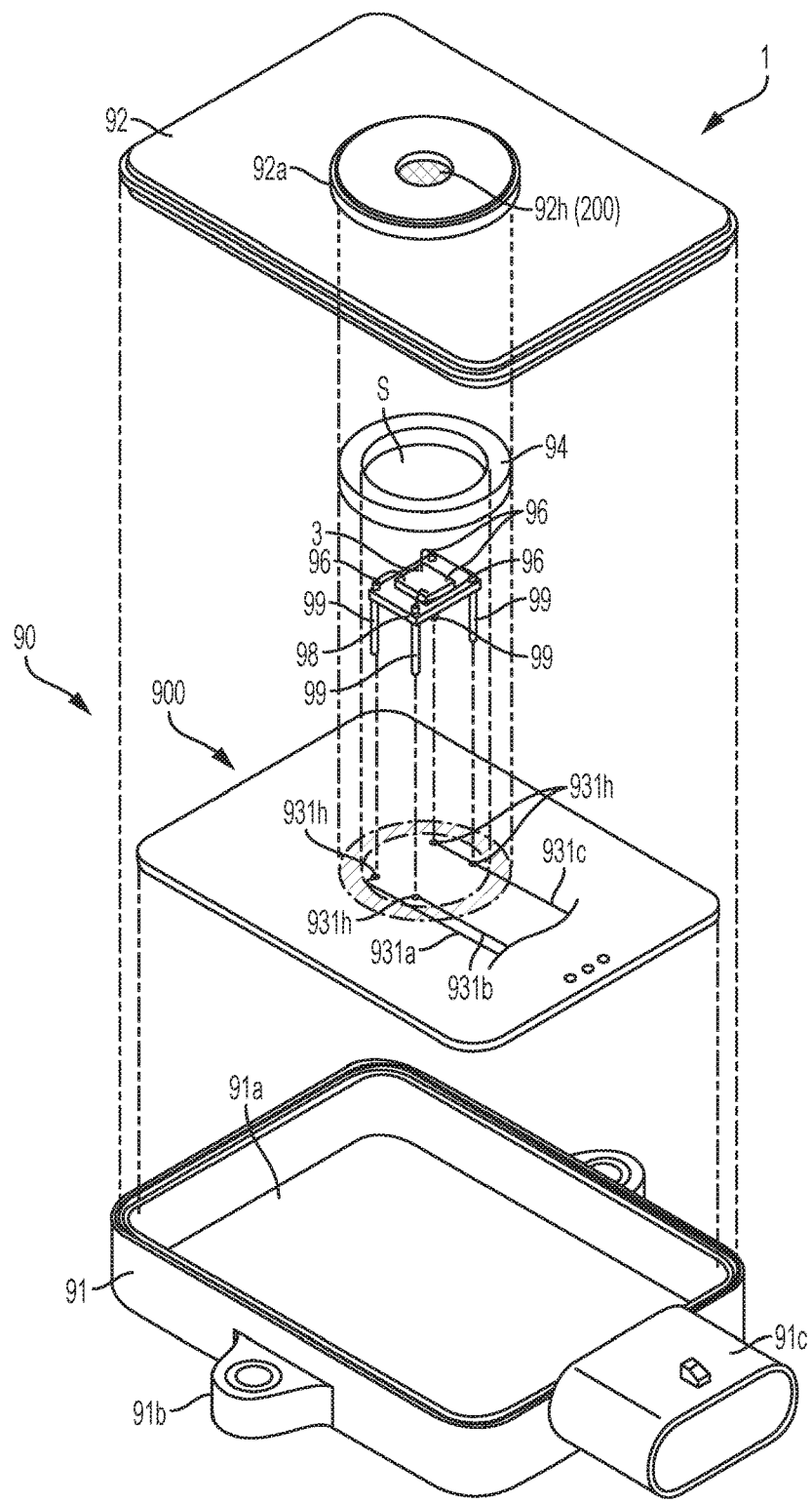
FIG. 4 is an exploded perspective view of the combustible gas detection apparatus with the gas detection element accommodated in a casing member.

FIG. 1 is a diagram showing the overall configuration of a combustible gas detection apparatus 1 to which the present invention is applied. FIG. 2 is a plan view showing the structure of a gas detection element 3 which is a main portion of the combustible gas detection apparatus 1 (the view also shows a part of the internal structure). FIG. 3 is a cross-sectional view of the gas detection element taken along line IIB-IIB in FIG. 2. FIG. 4 is an exploded perspective view of the combustible gas detection apparatus 1 with the gas detection element 3 accommodated in a casing member 90.

Overall Configuration

The combustible gas detection apparatus 1, which detects the concentration of a combustible gas using the thermal-conduction-type gas detection element 3, is disposed in, for example, the cabin of a fuel cell automobile for the purpose of, for example, detecting hydrogen leaks.

As shown in FIG. 1, the combustible gas detection apparatus 1 includes a control circuit 5 which drives and controls the gas detection element 3 (see FIGS. 2 and 3); a microcomputer 7 which generates a switching signal CG1 for controlling the operation of the control circuit 5 and performs various types of processing operations, including at least processing of computing the humidity of a combustible gas contained in an object gas (humidity computation), clogging determination processing which will be described below, and processing of computing the concentration of the combustible gas (gas concentration processing), based on detection signals V1 and SVT obtained from the control circuit 5; and a start switch 9 which starts and stops the control circuit 5 and the microcomputer 7 by establishing and cutting off a passage for supplying electric power from a DC power supply Vcc to the combustible gas detection apparatus 1.

The control circuit 5 (excluding a heat generation resistor 34 and a temperature measurement resistor 35 to be described below), the microcomputer 7, and the start switch 9 are formed on a single circuit board 900 (see FIG. 4), and the gas detection element 3 is formed separately from the circuit board 900.

Gas Detection Element

Next, the gas detection element 3 will be described.

As shown in FIGS. 2 and 3, the gas detection element 3 includes a flat base 30 (having a rectangular shape as viewed from above). A plurality of electrodes 31 are formed on one surface (hereinafter referred to as the "front surface") of the base 30, and a recess 301 is formed on the other surface (hereinafter referred to as the "back surface") of the base 30 near the center of the base 30 such that the recess 301 extends along one direction of the base 30.

The gas detection element 3 has a size of several millimeters in the length and width directions (e.g., 3 mm×3 mm), and is manufactured from a silicon substrate using, for example, a micromachining technique (micromachining process).

The electrodes 31 include two electrodes (electrode pads) 311 and 312 (hereinafter also referred to as the "first electrode group") disposed along one side (the lower side in FIG. 2) of the base 30 and two electrodes (electrode pads) 314 and 315 (hereinafter also referred to as the "second electrode group") disposed along the opposite side (the upper side in FIG. 3) of the base 30. Of these electrodes, the electrodes 312 and 315 are also referred to as the "ground electrodes" in the following description. The electrodes 31 are made of, for example, aluminum (Al) or gold (Au).

The base 30 includes a substrate 32 made of silicon and an insulating layer 33 formed on one surface of the substrate 32, and has a diaphragm structure. Specifically, the substrate 32 is partially removed such that the insulating layer 33 is partially exposed (through a substantially square opening in the present embodiment), whereby the above-mentioned recess 301 is formed. In the base 30, the side where the insulating layer 33 is present (where the substrate 32 is not removed) serves as the front surface of the base 30, and the side where the substrate 32 is present (including a region where the substrate 32 is partially removed) serves as the back surface of the base 30.

A heat generation resistor 34 in the form of a spiral pattern is embedded in a portion of the insulating layer 33 exposed to the back surface of the base 30 through the recess 301, and a temperature measurement resistor 35 used for temperature measurement is embedded along a long side (one side) of the base 30 on the side where the second electrode group (electrodes 314 and 315) is formed. Namely, the heat generation resistor 34 is supported by the insulating layer 33 to be located in a region closer to the center as compared with the temperature measurement resistor 35, and the temperature measurement resistor 35 is disposed in a region extending along one of the four sides which form the peripheral edge of the insulating layer 33.

The insulating layer 33 may be made of a single material or a composed of a plurality of layers made of different materials. Examples of the insulating material used for forming the insulating layer 33 include silicon oxide ($SiO_2$) and silicon nitride ($Si_3N_4$).

The heat generation resistor 34 is made of an electrically conductive material having a large temperature coefficient of resistance such that the resistance of the heat generation resistor 34 changes with a change in the temperature of the heat generation resistor 34 itself. The temperature measurement resistor 35 is made of an electrically conductive material selected such that the resistance of the temperature measurement resistor 35 changes in proportion to a change in temperature (in the present embodiment, the resistance increases as the temperature increases). The heat generation resistor 34 and the temperature measurement resistor 35 are made of the same resistor material (in the present embodiment, platinum (Pt)).

The heat generation resistor 34 is connected to the first electrode group (electrodes 311 and 312) through wiring lines 36 and wiring films 37 embedded so as to be located on the same plane as that on which the heat generation resistor 34 is formed. The temperature measurement resistor 35 is connected to the second electrode group (electrodes 314 and 315) through wiring films (not shown) embedded so as to be located on the same plane as that on which the temperature measurement resistor 35 is formed.

The wiring lines 36 and the wiring films 37 are made of the same resistor material as that used for forming the heat generation resistor 34 and the temperature measurement resistor 35. The electrodes 31 formed on the front surface of the base 30 are connected to the corresponding wring films 37 formed within the base 30 (the insulating layer 33) through contact holes (connection conductors).

Namely, one end of the heat generation resistor 34 is connected to the electrode 311 and the other end thereof is connected to the ground electrode 312; and one end of the temperature measurement resistor 35 is connected to the electrode 314 and the other end thereof is connected to the ground electrode 315.

Control Circuit

Next, the configuration of the control circuit 5 will be described.

As shown in FIG. 1, the control circuit 5 includes an energization control circuit 50 which controls the supply of electric current to the heat generation resistor 34 (hereinafter also referred to as "energization of the heat generation resistor 34") and outputs a detection signal V1 corresponding to the voltage across the heat generation resistor 34; and a temperature adjustment circuit 80 which supplies electric current to the temperature measurement resistor 35 and outputs a detection signal SVT which represents the temperature of the object atmosphere.

Energization Control Circuit

The energization control circuit 50 includes a bridge circuit (Wheatstone bridge circuit) 51 including the heat generation resistor 34; an amplification circuit 53 which amplifies the potential difference detected in the bridge circuit 51; and a current adjustment circuit 55 which adjusts (increases or decreases) the current flowing through the bridge circuit 51 in accordance with the output of the amplification circuit 53.

The current adjustment circuit 55 includes a transistor which is connected to a power line for supplying DC power supply voltage Vcc to the bridge circuit 51 and whose conduction state (ON-resistance) changes in accordance with an adjustment signal C output from the amplification circuit 53. Specifically, when the level of the adjustment signal C increases, the ON-resistance increases, and the current flowing through the bridge circuit 51 decreases. In contrast, when the level of the adjustment signal C decreases, the ON-resistance decreases and the current flowing through the bridge circuit 51 increases.

The amplification circuit 53 includes a well-known differential amplification circuit which is composed of an operational amplifier 531; fixed resistors 532 and 533 connected to the inverting input terminal and the non-inverting input terminal, respectively, of the operational amplifier 531; and a fixed resistor 534 and a capacitor 535 connected between the inverting input terminal and the output terminal of the operational amplifier 531.

Namely, when the voltage input to the non-inverting input terminal is larger than the voltage input to the inverting input terminal, the level of the adjustment signal C output from the amplification circuit 53 increases (thus, the current flowing through the bridge circuit 51 decreases); and when the voltage input to the non-inverting input terminal is smaller than the voltage input to the inverting input terminal, the level of the adjustment signal C decreases (thus, the current flowing through the bridge circuit 51 increases).

The bridge circuit 51 includes the heat generation resistor 34, two fixed resistors 511 and 512, and a variable resistor section 52 whose resistance can be switched. The fixed resistor 511 and the heat generation resistor 34 are connected in series, and the fixed resistor 512 and the variable resistor section 52 are connected in series. End portions PG of the series circuits located on the side where the heat generation resistor 34 and the variable resistor section 52 are provided are grounded, and the end portions of the series circuits located on the side where the fixed resistors 511 and 512 are provided are connected to the power supply side (the current adjustment circuit 55).

A connection node P+ between the fixed resistor 511 and the heat generation resistor 34 is connected to the non-inverting input terminal of the operation amplifier 531 through the fixed resistor 532. A connection node P− between the fixed resistor 512 and the variable resistor section 52 is connected to the inverting input terminal of the operation amplifier 531 through the fixed resistor 533. The potential at the connection node P+ is also supplied to the microcomputer 7 as the detection signal V1.

The variable resistor section 52 includes two fixed resistors 521 and 522 which differ in resistance, and a change-over switch 523 which enables one of the fixed resistors 521 and 522 in accordance with the switching signal CG1 from the microcomputer 7. The balance of the bridge circuit 51 can be changed by switching the resistance of the variable resistor section 52 by the changeover switch 523.

The fixed resistor 521 has a resistance such that the temperature of the heat generation resistor 34 becomes equal to the first set temperature CH (e.g., 400° C.), and the fixed resistor 522 has a resistance such that the temperature of the heat generation resistor 34 becomes equal to a second set temperature CL (e.g., 300° C.) lower than the first set temperature CH.

In the energization control circuit 50 configured as described above, when the supply of electric current from the DC power supply Vcc to the bridge circuit 51 is started, the amplification circuit 53 and the current adjustment circuit 55 adjust the current flowing through the bridge circuit 51 such that the potential difference between the connection nodes P+ and P− becomes zero. As a result, the resistance of the heat generation resistor 34 is controlled to a fixed value determined by the variable resistor section 52 (thus, the temperature of the heat generation resistor 34 is controlled to the first set temperature CH or the second set temperature CL).

Specifically, in the case where the amount of the combustible gas within the object atmosphere changes and the amount of heat removed by the combustible gas becomes greater than the amount of heat generated by the heat generation resistor 34, the resistance of the heat generation resistor 34 decreases as its temperature falls. In contrast, in the case where the amount of heat removed by the combustible gas becomes smaller than the amount of heat generated by the heat generation resistor 34, the resistance of the generation resistor 34 increases as its temperature rises.

When the resistance of the generation resistor 34 decreases, the amplification circuit 53 and the current adjustment circuit 55 increase the current flowing through the bridge circuit 51 to thereby increase the amount of heat generated by the heat generation resistor 34. In contrast, when the resistance of the generation resistor 34 increases, the amplification circuit 53 and the current adjustment circuit 55 decrease the amount of current flowing through the bridge circuit 51 to thereby decrease the amount of heat generated by the heat generation resistor 34. Thus, the heat generation resistor 34 is controlled to have a fixed (constant) resistance (accordingly, a fixed (constant) temperature).

Namely, the magnitude of the current flowing through the heat generation resistor 34; i.e., the amount of heat required to maintain the temperature (resistance) of the heat generation resistor 34 constant (more particularly, the amount of heat removed by the combustible gas) can be determined from the detection signal V1, which represents the potential at the connection node P+. Since the required amount of heat changes with the gas concentration, the concentration of the combustible gas can be determined from the detection signal V1. Specifically, when the gas concentration is calculated, a correction is performed using the humidity H of the object atmosphere, and the degree of clogging of the gas inlet opening 92h, which will be described below, is determined using the humidity H. This will be described in the section on fitted "gas concentration computation processing," the section "humidity computation processing," and the section "clogging determination processing" provided below.

Temperature Measurement Circuit

The temperature adjustment circuit 80 includes a bridge circuit (Wheatstone bridge circuit) 81 including the temperature measurement resistor 35; and an amplification circuit 83 which amplifies the potential difference obtained from the bridge circuit 81.

The amplification circuit 83 includes a well-known differential amplification circuit which is composed of an operational amplifier 831; fixed resistors 832 and 833 connected to the inverting input terminal and the non-inverting input terminal, respectively, of the operational amplifier 831; and a fixed resistor 834 and a capacitor 835 connected between the inverting input terminal and the output terminal of the operational amplifier 831.

The bridge circuit 81 includes the temperature measurement resistor 35 and three fixed resistors 811, 812, and 813. The fixed resistor 811 and the temperature measurement resistor 35 are connected in series, and the fixed resistor 812 and the fixed resistor 813 are connected in series. End portions of these series circuits located on the side where the temperature measurement resistor 35 and the fixed resistor 813 are provided are grounded, and end portions of these series circuits located on the side where the fixed resistors 811 and 812 are provided are connected to the power supply.

A connection node P− between the fixed resistor 811 and the temperature measurement resistor 35 is connected to the inverting input terminal of the operational amplifier 531 through the fixed resistor 833. A connection node P+ between the fixed resistors 812 and 813 is connected to the non-inverting input terminal of the operational amplifier 831 through the fixed resistor 832. The output of the operational amplifier 831 is supplied to the microcomputer 7 as the temperature detection signal SVT.

The temperature measurement resistor 35 is set such that when the temperature of the object atmosphere to which the gas detection element 3 is exposed is equal to a reference temperature set in advance, the temperature detection signal SVT assumes a reference value.

When the temperature of the object atmosphere changes, the resistance of the temperature measurement resistor 35 changes. As a result, a potential difference is produced, and a voltage obtained by amplifying the potential difference is output as the temperature detection signal SVT.

Notably, when the gas detection element 3 is connected to the control circuit 5, the electrodes 31 (311, 312, 314, 315) of the gas detection element 3 are connected such that the electrode 311 is connected to the connection node P+ of the energization control circuit 50, the electrode 314 is connected to the connection node P− of the temperature adjustment circuit 80, and the ground electrodes 312 and 315 are connected to the common ground line of the control circuit 5.

Microcomputer

The microcomputer 7 is a well-known microcomputer which includes a storage device 8 (ROM, RAM, etc.) which stores various program and data for executing the humidity computation processing, the clogging determination processing, the gas concentration computation processing, etc.; a CPU which executes the programs stored in the storage device 8; an IO port for inputting and outputting various signals; a timer for clocking time; etc.

Here, the signal level of the detection signal V1 detected when the temperature of the heat generation resistor 34 is the first set temperature CH (400° C.) will be referred to as a high-temperature-time voltage VH; the signal level of the detection signal V1 detected when the temperature of the heat generation resistor 34 is the second set temperature CL (300° C.) will be referred to as a low-temperature-time voltage VL; and the signal level of the temperature detection signal SVT received from the temperature adjustment circuit 80 will be referred to as a temperature voltage VT.

The storage device 8 stores temperature conversion data which represents the correlation between the environmental temperature T within the object atmosphere and the temperature voltage VT; humidity conversion data which represents the correlation between the humidity H of the object atmosphere and the high-temperature-time voltage VH, the low-temperature-time voltage VL, and the temperature voltage VT; and concentration conversion data which represents the correlation between the high-temperature-time voltage VH or the low-temperature-time voltage VL (in the present embodiment, the high-temperature-time voltage VH is used) and the concentration X of the combustible gas. Specifically, each conversion data set represents a conversion map, a calculation formula for conversion, or the like, which is prepared in advance based on the data obtained through an experiment or the like.

The humidity conversion data includes voltage ratio conversion map data which represents the correlation between the environmental temperature T (thus, the temperature voltage VT) and the voltage ratio VC(0) to be described below; and humidity conversion map data which represents the correlation between the voltage ratio difference ΔVC to be described below and the humidity H. The concentration conversion data includes high-temperature-time voltage conversion map data which represents the correlation between the temperature voltage VT and the high-temperature-time voltage VH(0) to be described below; humidity voltage change conversion map data which represents the correlation between the high-temperature-time voltage VH and the humidity H, and the high-temperature-time voltage change ΔVH(H) to be described below; and gas sensitivity conversion map data which represents the correlation between the temperature voltage VT and the high-temperature-time voltage VH, and the gas sensitivity G(VT) to be described below.

When electric current is supplied from the DC power supply Vcc to the microcomputer 7 as a result of the start switch 9 being turned on, the microcomputer 7 starts its operation. The CPU of the microcomputer 7 initializes various portions thereof and then starts the gas concentration computation processing.

Notably, the energization control circuit 50 and the microcomputer 7 which outputs the switching signal CG1 correspond to the energization control section. The microcomputer 7 which performs the humidity computation processing, the clogging determination processing, and the gas concentration computation processing corresponds to the humidity computation section, the clogging determination section, and the gas concentration computation section.

Next, the structure of the casing member 90 of the combustible gas detection apparatus 1 will be described with reference to FIG. 4.

As shown in FIG. 4, the combustible gas detection apparatus 1 includes the gas detection element 3, the circuit board 900, and the casing member 90 for accommodating the gas detection element 3 and the circuit board 900. The casing member 90 has a casing body portion 91 and a generally flat-plate-shaped top plate 92 for closing an upper opening 91a of the casing body portion 91.

Flanges 91b extend outward from central portions of the two long sides of the casing body portion 91, and a predetermined bolt hole is formed in each flange portion 91b at the center thereof. Bolts (not shown) passing through the bolt holes are screwed into an object to which the combustible gas detection apparatus 1 is to be attached (for example, a predetermined portion of a vehicle), whereby the combustible gas detection apparatus 1 is attached to the object. A tubular connector portion 91c for exchanging signals with an external device extends outward from one short side of the casing body portion 91.

An annular member 92a projects upward from a central portion of the top plate 92, and a gas inlet opening 92h is provided on the radially inner side of the annular member 92a. An object atmosphere flows between the space inside the casing member 90 and the space outside the casing ember 90 through the gas inlet opening 92h. The gas inlet opening 92h is covered with wire gauze 200.

The combustible gas detection apparatus 1 is a hydrogen gas sensor for measuring the hydrogen concentration of the object atmosphere. The metal gauze 200 serves a flame arrester for preventing flame from escaping to the outside of the casing member 90 even when the temperature of the gas detection element 3 disposed inside the casing member 90 exceeds the temperature at which hydrogen gas ignites.

Notably, a water repellent filter may be disposed on the lower side of the metal gauze 200 (on the side toward the internal space of the casing member 90) such that the gas inlet opening 92h is covered with the filter, to thereby prevent water from entering the internal space of the casing member 90 through the gas inlet opening 92h. Alternatively, the water repellent filter may be disposed on the upper side of the metal gauze 200 such that the gas inlet opening 92h is covered with the filter.

The gas detection element 3 is disposed (mounted) on the upper surface of the circuit board 900 via a pedestal 98. A plurality of (four in this example) electrodes of the gas detection element 3 are connected, through bonding wires 96, to corresponding connection terminals 99 projecting downward from the four corners of the pedestal 98. When the circuit board 900 is positioned and accommodated in the casing body portion 91 and the top plate 92 is fitted to the inner edge of the upper opening 91a of the casing body portion 91, an annular elastic seal member 94 bonded to the back surface of the top plate 92 is pressed against the upper surface of the circuit board 900, whereby the circuit board 900 is fixed.

The above-described control circuit 5 (excluding the heat generation resistor 34 and the temperature measurement resistor 35, which will be described below) for controlling the gas detection element 3, the microcomputer 7, the start switch 9, and various electronic parts (not shown) are mounted on the circuit board 900 by means of soldering or the like. The circuit board 900 has a plurality of wiring traces 931a to 931c formed thereon for electrical connection with the gas detection element 3, and four through holes 931h are formed at ends of the wiring traces 931a to 931c. The connection terminals 99 are inserted into the through holes 931h, whereby the gas detection element 3 is electrically connected to the circuit board 900. The wiring traces 931a to 931c are extended to the outside through the connector portion 91c.

The internal space of the casing member 90 surrounded by the surface of the circuit board 900, the gas inlet opening 92h, and the inner side surface of the elastic seal member 94 forms a measurement chamber S which the gas detection element 3 faces and which communicates with the object atmosphere. The hydrogen gas concentration of the object atmosphere within the measurement chamber S is detected by the gas detection element 3. In the present embodiment, the top plate 92 is fixed to the casing body portion 91 by means of an adhesive or welding.

Gas Concentration Computation Processing, Humidity Computation Processing, and Clogging Determination Processing Next, the gas concentration computation processing, the humidity computation processing, and the clogging determination processing of the combustible gas detection apparatus according to the first embodiment of the present invention will be described with reference to FIGS. 5 to 9.

Figure 5A:
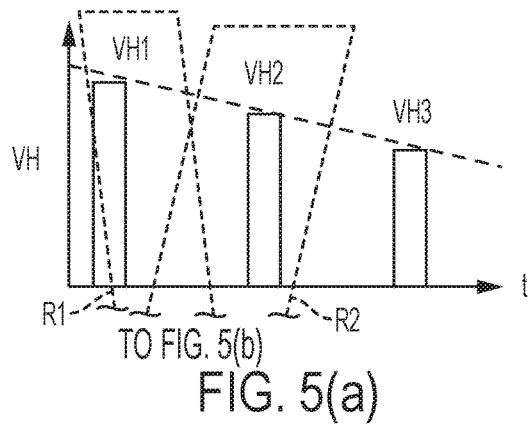
FIGS. 5($a$) to 5($d$) are diagrams relating to the first embodiment.
Figure 5B:
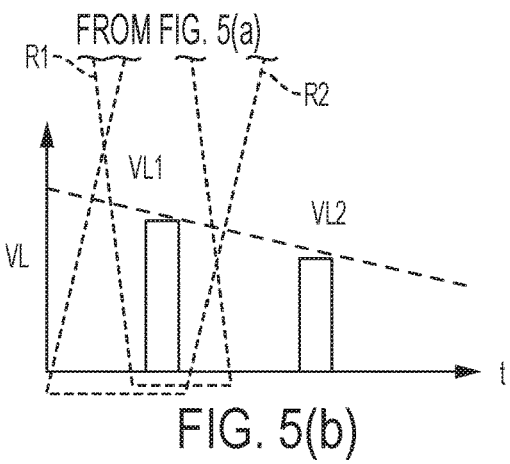
Figure 5C:
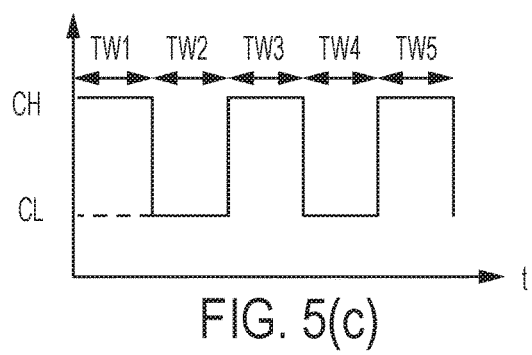
Figure 5D:
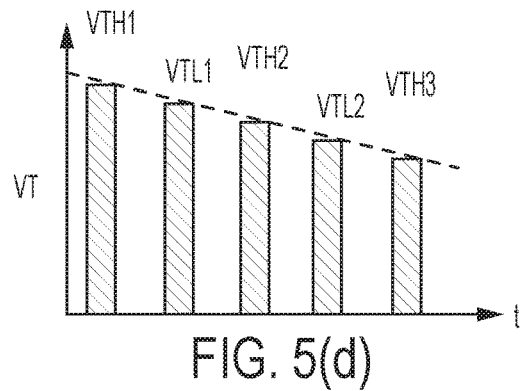
Figure 6:
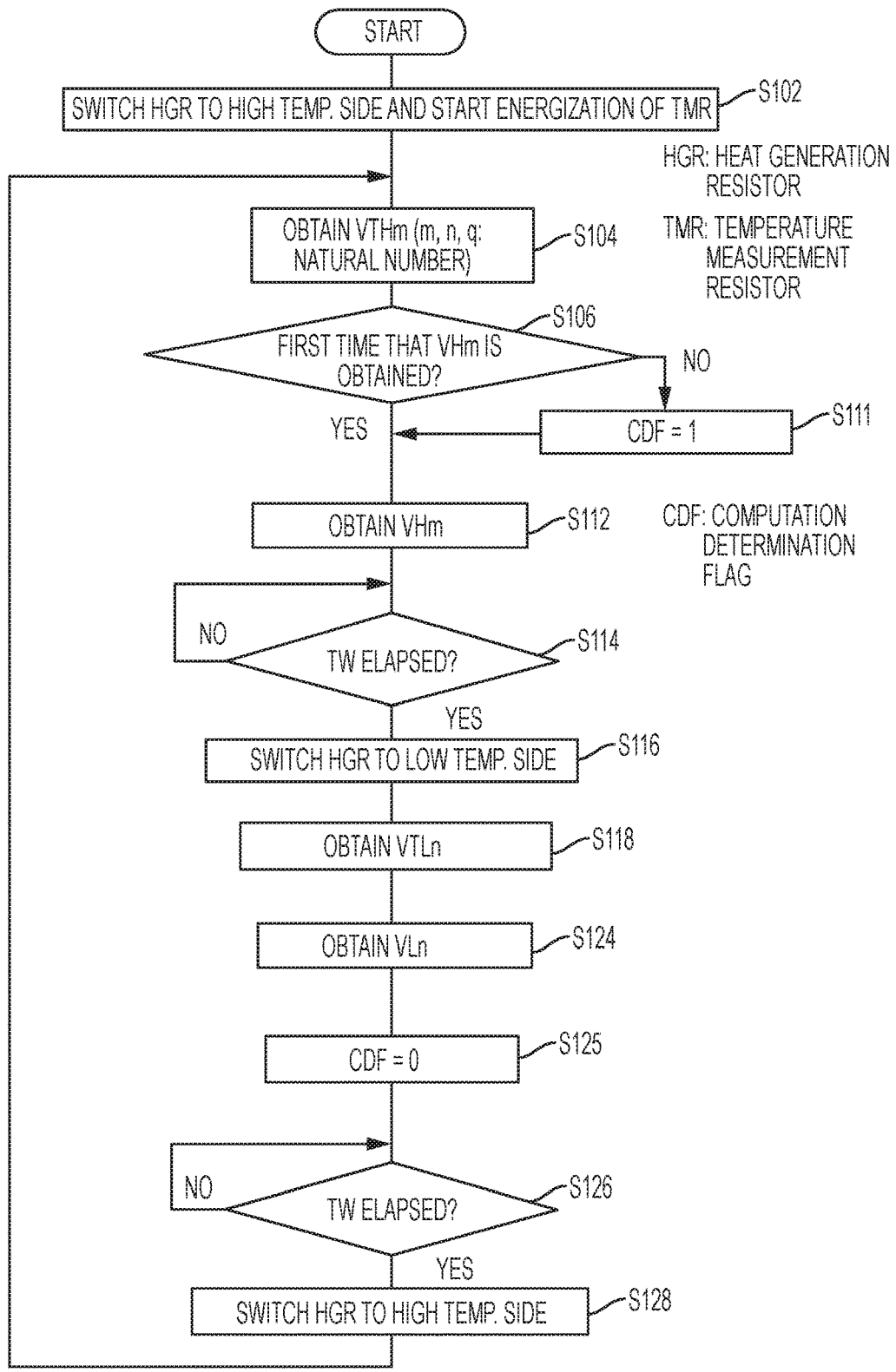
FIG. 6 is a flowchart relating to the first embodiment, and showing a process of obtaining VH, VL, and VT.
Figure 7:
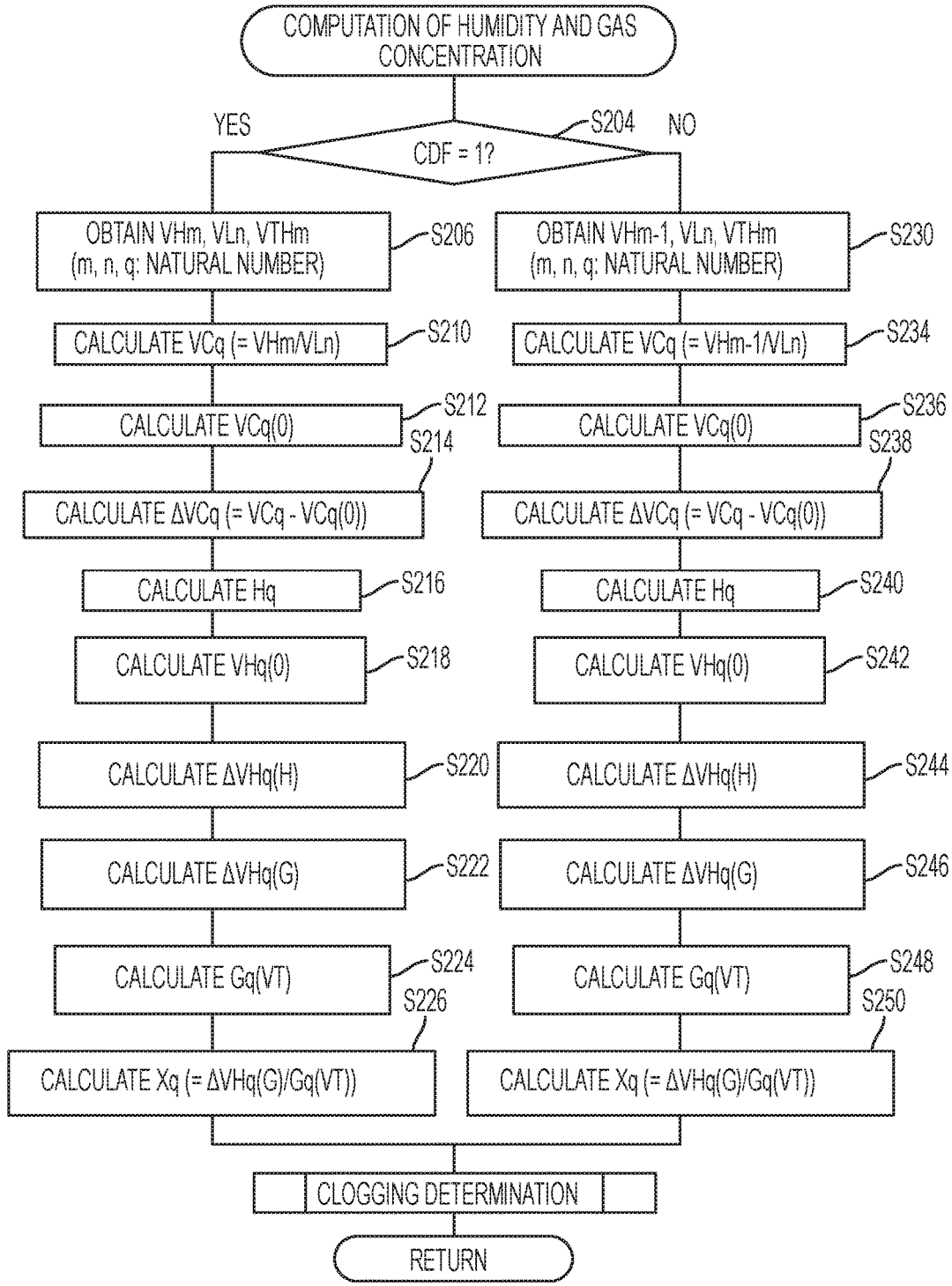
FIG. 7 is a flowchart relating to the first embodiment, and showing humidity computation processing and gas concentration computation processing.
Figure 8:
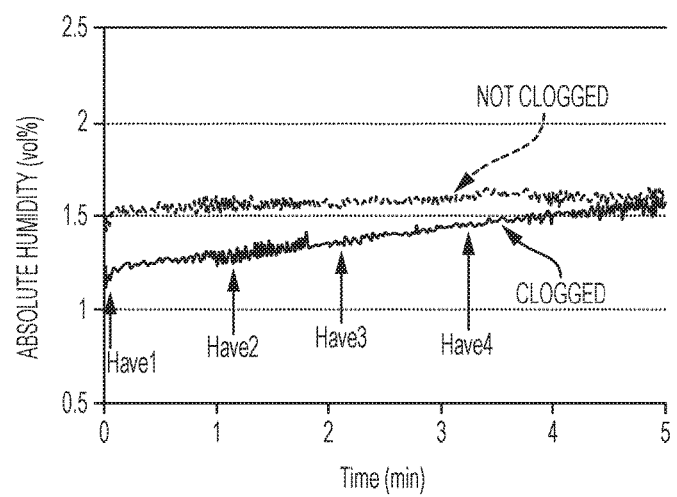
FIG. 8 is a diagram relating to the first embodiment, and showing the concept of clogging determination processing.
Figure 9:
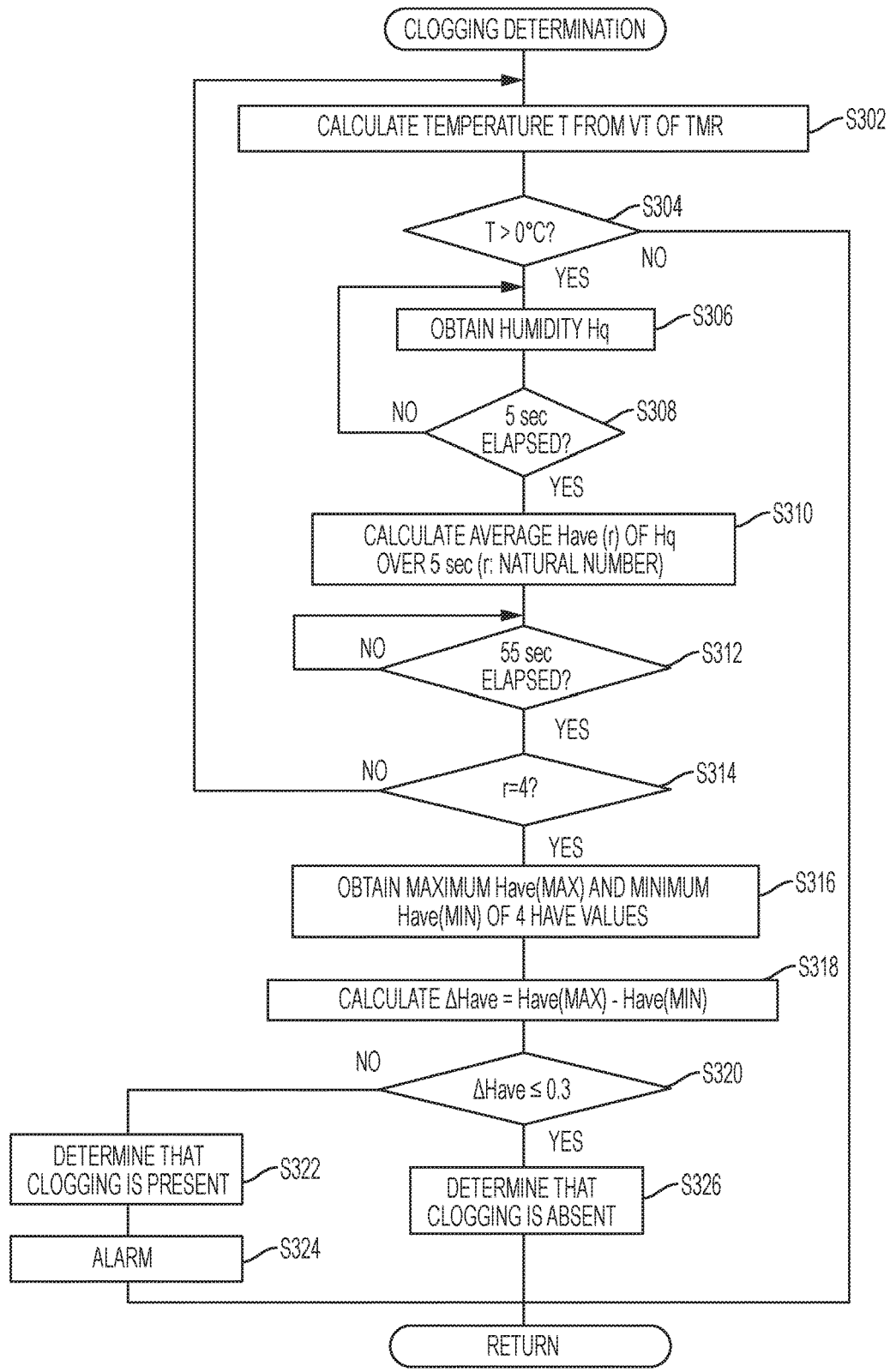
FIG. 9 is a flowchart relating to the first embodiment, and showing the clogging determination processing.

FIG. 5 represents time charts (FIGS. 5(a) and 5(b)) showing timings at which VH and VL are obtained, a time chart (FIG. 5(c)) showing the first set temperature (CH) and the second set temperature (CL) of the heat generation resistor, and a time chart (FIG. 5(d)) showing timings at which the temperature of the temperature measurement resistor (temperature voltage VT) is obtained. FIG. 6 is a flowchart showing processing of obtaining VH, VL, and VT. FIG. 7 is a flowchart showing the humidity computation processing and the gas concentration computation processing. FIG. 8 is a diagram showing the concept of the clogging determination processing. FIG. 9 is a flowchart showing the clogging determination processing.

As shown in FIGS. 5(a) and 5(b), a high-temperature-time voltage VH and a low-temperature-time voltage VL at two set temperatures (the first set temperature and the second set temperature) are obtained alternately at predetermined time intervals (every time a predetermined period of time elapses). Specifically, after detection of VH1 in the first time period TW1, VL1 is detected in the next time period TW2. For calculating the ratio of VH to VL at this time, VH1 and VL1 in a region R1 shown in FIG. 5 are used. Subsequently, after detecting the above-mentioned VL1, VH2 is detected in the next time period TW3. For calculating the ratio of VH to VL at this time, VL1 and VH2 in a region R2 shown in FIG. 5 are used.

Notably, in FIG. 5, the values of the high-temperature-time voltage (VH) are detected chronologically in the order of suffixes 1, 2, 3 for the high-temperature-time voltage (VH). Similarly, the values of the low-temperature-time voltage (VL) are detected chronologically in the order of suffixes 1, 2, 3 for the low-temperature-time voltage (VL). A temperature voltage VTL represents a temperature voltage (VT) which is detected in the same time period as the time period in which the corresponding low-temperature-time voltage (VL) is detected. A temperature voltage VTH represents a temperature voltage (VT) which is detected in the same time period as the time period in which the corresponding high-temperature-time voltage (VH) is detected.

Also, as described above, in the region R1 extending across the time periods TW1 and TW2, a voltage ratio VC1 (which will be described below) is obtained from the high-temperature-time voltage VH1 and the low-temperature-time voltage VL1. Next, in the region R2 extending across the time periods TW2 and TW3, a voltage ratio VC2 is obtained from the low-temperature-time voltage VL1 and the high-temperature-time voltage VH2. As a result, the voltage ratio of VH to VL can be obtained for each time period TW. In contrast, in the case where, after the region R1 for example, the next voltage ratio is obtained from the high-temperature-time voltage VH2 and the low-temperature-time voltage VL2 in time periods TW3 and TW4, the intervals between calculation timings become double the length of the time periods.

The humidity of the object atmosphere and the gas concentration are computed based on the voltage ratio.

Notably, when the gas concentration is computed using the voltage ratio VC, an environmental temperature in the time period TW1 (temperature voltage VTH1) or an environmental temperature in the time period TW2 (temperature voltage VTL1) may be used as an environmental temperature. However, when the latest environmental temperature (namely, VTL1 in the region R1, VTH2 in the region R2) is used, the gas concentration can be computed using the latest environmental temperature. Therefore, use of the latest environmental temperature is preferred.

FIG. 5(*d*) shows a typical temperature change within a short period of time (for example, 10 minutes or shorter) after the startup of the combustible gas detection apparatus 1. In general, when the combustible gas detection apparatus 1 is started, the temperature of the object atmosphere within the combustible gas detection apparatus 1 rises and reaches a certain temperature within about 10 minutes.

Next, the processing of obtaining VH, VL, and VT, the gas concentration computation processing, and the humidity computation processing, which are executed by the CPU of the microcomputer 7, will be described with reference to FIGS. 6 and 7.

Notably, the gas concentration X may be obtained from the low-temperature-time voltage VL or the high-temperature-time voltage VH while using the concentration conversion data and correcting the obtained gas concentration X by the environmental temperature T obtained from the temperature voltage VT while using the temperature conversion data. However, in the present embodiment, the gas concentration X is obtained using the humidity H in addition to the environmental temperature T. Also, in the present embodiment, the humidity H is calculated from the voltage ratio of VH to VL in successive time periods.

As shown in FIG. 6, in the processing of obtaining VH, VL, and VT, in step S102, the CPU first switches the heat generation resistor 34 to the high temperature side (the first set temperature (CH) side) and starts the supply of electric current to the temperature measurement resistor 35. Specifically, by using the switching signal CG1, the CPU maintains the resistance of the bridge circuit 51 at a value corresponding to the first set temperature CH; i.e., maintains the temperature of the heat generation resistor 34 at the first set temperature CH, within the predetermined time period TW.

Next, in S104, the CPU obtains a temperature voltage VTHm in the time period of S102. Notably, FIG. 5(*c*) is a time chart showing the temperature of the heat generation resistor, and FIG. 5(*d*) is a time chart showing timings at which the temperature voltage VT is obtained. Each of suffixes m, n (which will be described below), and q (which will be described below) is a natural number, and shows that values with these suffixes are obtained chronologically in the order of 1, 2, 3 (this rule also applies to the following description).

Next, in S106, the CPU determines whether or not the high-temperature-time voltage (VHm) is being obtained for the first time; i.e., whether or not the high-temperature-time voltage is VH1. In the case where the result of the determination is No, the CPU sets a computation determination flag to 1 (S111). The CPU then proceeds from S111 to S112 and obtains the high-temperature-time voltage (VHm) of the heat generation resistor 34. Meanwhile, in the case where the result of the determination in S106 is Yes, the CPU proceeds directly to S112.

Notably, the computation determination flag is a flag which is used in the processing shown by the flowchart of FIG. 7 (which will be described below) so as to determine which values of VH and VL are obtained (for example, the values of VH and VL in the region R1 or the values of VH and VL in the region R2). In the case where the computation determination flag=1, the CPU performs processing of obtaining the values of VH and VL corresponding to the region R2.

Next, the CPU determines whether or not the time period TW has elapsed (S114). In the case where the result of the determination in S114 is Yes, the CPU proceeds to S116. In the case where the result of the determination in S114 is No, the CPU returns to S114 and waits until the time period TW elapses. Notably, in the example of FIGS. 6 and 7, TW=200 msec.

Next, in S116, the CPU switches the heat generation resistor 34 to the low temperature side (the second set temperature (CL) side) and obtains the temperature voltage VTLn in the time period of S116 (S118).

Next, the CPU obtains the low-temperature-time voltage (VLn) of the heat generation resistor 34 in S124 and sets the computation determination flag to 0 in S125.

Next, the CPU determines whether or not the time period TW has elapsed (S126). In the case where the result of the determination in S126 is Yes, the CPU proceeds to S128. In the case where the result of the determination in S126 is No, the CPU returns to S126 and waits until the time period TW elapses.

In S128, the CPU switches the heat generation resistor 34 to the high temperature side (the first set temperature (CH) side), and returns to S104.

The values of VHm, VLn, VTHm, and VTLn obtained as described above are stored in the storage device 8 (RAM) and are read out in the gas concentration computation processing and the humidity computation processing which will be described below.

Next, the humidity computation processing and the gas concentration computation processing will be described with reference to FIG. 7. Notably, the humidity computation processing and the gas concentration computation processing are performed for each time period TW. Namely, since the section of S104 to S114 of FIG. 6 is performed in a certain time period TW, the humidity computation processing and the gas concentration computation processing are performed at a point in time after S114. Further, the section of S116 to S126 is performed in the next time period TW, and the next humidity computation processing and the next gas concentration computation processing are performed at a point in time after S126.

In S204 of FIG. 7, the CPU first determines whether or not the computation determination flag is 1. In the case where the result of the determination in S204 is Yes (namely, the last processing of FIG. 6 is the processing of obtaining the high-temperature-time voltage VHm in S104 to S114), the CPU proceeds to S206, and obtains VHm and VLn from the energization control circuit 50 and obtains VTHm from the temperature adjustment circuit 80. The case where m=2 and n=1 corresponds to the region R2 of FIG. 5, and the CPU computes the humidity and the gas concentration based on the high-temperature-time voltage VHm, the low-temperature-time voltage VLn, and the temperature voltage VTHm in the time period in which the high-temperature-time voltage VHm is obtained.

Meanwhile, in the case where the result of the determination in S204 is No, since the last processing of FIG. 6 is the processing of obtaining the low-temperature-time voltage VLn in S118 to S126 as will be described below, the CPU computes the humidity and the gas concentration based on the high-temperature-time voltage VHm−1, the low-temperature-time voltage VLn, and the temperature voltage VTLn in the time period in which the low-temperature-time voltage VLn is obtained.

Next, in step S210, the CPU calculates a voltage ratio VCq in accordance with the following equation (2) while using as input values of the equation (2) the VLn and VHm obtained in step S206.

$$VCq = VHm/VLn \qquad (2)$$

Next, in step S212, the CPU calculates a voltage ratio $VCq(0)$ at the environmental temperature THm (i.e., the temperature voltage VTHm) for the case where the gas concentration X is zero and the humidity H is zero based on the temperature voltage VTHm obtained in step S206 and the voltage ratio conversion map data.

In step S214, the CPU calculates a voltage ratio difference $\Delta VCq$ at the environmental temperature THm (i.e., the temperature voltage VTHm) in accordance with the following equation (3) while using as input values of the equation (3) the voltage ratio VCq calculated in step S210 and the VCq(0) calculated in step S212.

$$\Delta VCq = VCq - VCq(0) \tag{3}$$

Next, in step S216, the CPU calculates a humidity Hq corresponding to the voltage ratio difference $\Delta VCq$ based on the voltage ratio difference $\Delta VCq$ calculated in step S214 and the humidity conversion map data. S206 to S216 correspond to the "humidity computation processing."

In step S218, the CPU calculates a high-temperature-time voltage VHq(0) at the environmental temperature THm (i.e., the temperature voltage VTHm) for the case where the gas concentration X is zero and the humidity H is zero from the VTHm and VHm obtained in step S206 and the high-temperature-time voltage conversion map data.

Subsequently, in step S220, the CPU calculates a high-temperature-time voltage change $\Delta VHq(H)$, which represents a change in the VHm (voltage change amount) caused by the humidity Hq, based on the VHm obtained in step S206, the humidity Hq calculated in step S216, and the humidity voltage change conversion map data.

In step S222, the CPU calculates a high-temperature-time voltage change $\Delta VHq(G)$, which represents a change in the VHm (voltage change amount) caused by the combustible gas in accordance with the following equation (4) while using as input values of the equation (4) the VHm obtained in step S206, the VHq(0) calculated in step S218, and the $\Delta VHq(H)$ calculated in step S220.

$$\Delta VHq(G) = VHm - VHq(0) - \Delta VHq(H) \tag{4}$$

Subsequently, in step S224, the CPU calculates, based on the VTHm and VHm obtained in step S206 and the gas sensitivity conversion map data, a gas sensitivity Gq(VT) which represents the sensitivity for the combustible gas (unit is the reciprocal of the gas concentration X) which is set in advance for the VHm, the setting being performed for each of different values of the environmental temperature THm (i.e., the temperature voltage VTHm).

Finally, in step S226, the CPU calculates the gas concentration Xq (the concentration of the combustible gas) in accordance with the following equation (5) while using as input values of the equation (5) the high-temperature-time voltage change $\Delta VHq(G)$ calculated in step S222 and the gas sensitivity Gq(VT) calculated in step S224. Subsequently, the CPU proceeds to the later-described clogging determination processing which is a subroutine and then ends the present gas concentration computation processing.

$$Xq = \Delta VHq(G)/Gq(VT) \tag{5}$$

Meanwhile, in the case where the result of the determination in S204 is No (namely, the last processing of FIG. 6 is the processing of obtaining the low-temperature-time voltage VLn in S116 to S126, the CPU proceeds to S230, and obtains VHm−1 and VLn from the energization control circuit 50 and obtains VTLn from the temperature adjustment circuit 80. The case where m=2 and n=2 corresponds to the region R1 of FIG. 5.

Next, in step S234, the CPU calculates a voltage ratio VCq in accordance with the following equation (7) while using as input values of the equation (7) the VHm−1 and VLn obtained in step S230.

$$VCq = VHm-1/VLn \tag{7}$$

Although the suffix q is a natural number which increases chronologically, it is not a value interlocked directly with m and n. Therefore, the values with the suffix q are not denoted with "q+1" or the like, and are all denoted with "q." For example, when a voltage ratio VC1(q=1) is obtained by the processing in S206 and steps subsequent thereto and the result of the determination in S204 becomes No, a voltage ratio VC2(q=2) is obtained by the processing in S230 and steps subsequent thereto, and the value of q increases by one every time a new voltage ratio is calculated.

In step S236, the CPU calculates a voltage ratio VCq(0) at the environmental temperature TLn (i.e., the temperature voltage VTLn) for the case where the gas concentration X is zero and the humidity H is zero based on the temperature voltage VTLn obtained in step S230 and the voltage ratio conversion map data.

In step S238, the CPU calculates a voltage ratio difference $\Delta VCq$ at the environmental temperature TLn (i.e., the temperature voltage VTLn) in accordance with the following equation (8) while using as input values of the equation (8) the voltage ratio VCq calculated in step S234 and the VCq(0) calculated in step S236.

$$\Delta VCq = VCq - VCq(0) \tag{8}$$

Next, in step S240, the CPU calculates a humidity Hq corresponding to the voltage ratio difference $\Delta VCq$ based on the voltage ratio difference $\Delta VCq$ calculated in step S238 and the humidity conversion map data.

In step S242, the CPU calculates a high-temperature-time voltage VHq(0) at the environmental temperature TLn (i.e., the temperature voltage VTLn) for the case where the gas concentration X is zero and the humidity H is zero from the VTLn and VHm−1 obtained in step S230 and the high-temperature-time voltage conversion map data.

Subsequently, in step S244, the CPU calculates a high-temperature-time voltage change $\Delta VHq(H)$, which represents a change in the VHm−1 (voltage change amount) caused by the humidity Hq, based on the VHm−1 obtained in step S230, the humidity Hq calculated in step S240, and the humidity voltage change conversion map data.

In step S246, the CPU calculates a high-temperature-time voltage change $\Delta VHq(G)$, which represents a change in the VHm−1 (voltage change amount) caused by the combustible gas in accordance with the following equation (9) while using as input values of the equation (9) the VHm−1 obtained in step S230, the VHq(0) calculated in step S242, and the $\Delta VHq(H)$ calculated in step S244.

$$\Delta VHq(G) = VHm-1 - VHq(0) - \Delta VHq(H) \tag{9}$$

Subsequently, in step S248, the CPU calculates, based on the VTLn and VHm−1 obtained in step S230 and the gas sensitivity conversion map data, a gas sensitivity Gq(VT) which represents the sensitivity for the combustible gas (unit is the reciprocal of the gas concentration X) which is set in advance for the VHm−1, the setting being performed for each of different values of the environmental temperature TLn (i.e., the temperature voltage VTLn).

Finally, in step S250, the CPU calculates the gas concentration Xq (the concentration of the combustible gas) in accordance with the following equation (10) while using as input values of the equation (10) the high-temperature-time voltage change ΔVHq(G) calculated in step S246 and the gas sensitivity Gq(VT) calculated in step S248. Subsequently, the CPU proceeds to the later-described clogging determination processing which is a subroutine and then ends the present gas concentration computation processing.

$$Xq = \Delta VHq(G)/Gq(VT) \quad (10)$$

As described above, in the processing of FIGS. 6 and 7, by outputting the switching signal CG1 to the changeover switch 523 every time the time period TW elapses, the electrical path extending from the connection node P-between the fixed resistor 512 and the variable resistor section 52 to the end portion PG (the ground-side end portion of the variable resistor section 52) (the electrical path within the variable resistor section 52) is switched such that the fixed resistors 521 and 522 are alternately inserted into the electrical path. Thus, the high-temperature-time voltage VHm-1, VHm, the low-temperature-time voltage VLn, and the temperature voltage VTLn, VTHm are obtained. In the humidity computation processing and the gas concentration computation processing, the environmental temperature TLn, THm is computed from the temperature voltage VTLn, VTHm.

Further, the humidity Hq of the object atmosphere is computed from the voltage ratio of the high-temperature-time voltage (VHm-1, VHm) to the low-temperature-time voltage VLn, and the gas concentration Xq is corrected using the environmental temperature TLn, THm and the humidity Hq.

Next, the concept of the clogging determination processing according to the first embodiment will be described with reference to FIG. 8.

FIG. 8 shows an actually measured time-course change in the absolute humidity within the combustible gas detection apparatus 1 after the combustible gas detection apparatus was started (key on) for the case where the gas inlet opening 92h of the combustible gas detection apparatus 1 was intentionally clogged and the case where the gas inlet opening 92h was not clogged.

In the case where the gas inlet opening 92h was "not clogged," the time-course change in the absolute humidity within the combustible gas detection apparatus 1 was small and approximately constant (about 1.5 vol %). Meanwhile, in the case where the gas inlet opening 92h was "clogged," the absolute humidity immediately after the startup (key on) was smaller than that in the case where the gas inlet opening 92h was "not clogged." However, the absolute humidity increased with time and approached, within about 5 minutes, the value observed in the case where the gas inlet opening 92h was "not clogged". Conceivably, this phenomenon occurs for the following reason. As shown in FIG. 5(d), when the combustible gas detection apparatus 1 is started, the temperature of the object atmosphere within the combustible gas detection apparatus 1 increases, whereby adhering water or the like within the apparatus 1 evaporates. However, since the gas inlet opening 92h is closed, the humidity within the apparatus 1 increases. When the temperature of the object atmosphere reaches a predetermined temperature, the humidity within the apparatus 1 stops rising and becomes constant.

In view of the above, it is possible to determine whether or not the gas inlet opening is clogged by determining, within a predetermined time (in the present example, 3 minutes) after the startup (key on) of the combustible gas detection apparatus, whether or not the time-course change in the humidity is equal to or smaller than a first threshold (in the present example, 0.3 vol % (absolute humidity)).

Notably, as shown in FIG. 8, in the first embodiment, four humidity data sets Have1 to Have4 are obtained immediately after the startup, after elapse of one minute, after elapse of two minutes, and after elapses of three minutes, respectively, and the time-course change is obtained from the four humidity data sets.

Next, the clogging determination processing which is a subroutine based on the concept of FIG. 8 will be described with reference to FIG. 9.

First, in S302, the CPU obtains the temperature voltage VT of the temperature measurement resistor 35 and calculates the temperature T. Subsequently, in S304, the CPU determines whether or not the temperature T exceeds 0° C. In the case where the result of the determination in S304 is Yes, the CPU proceeds to S306. In the case where the result of the determination in S304 is No, the CPU ends the processing of the subroutine and returns to the main routine. This is because, when the temperature T is 0° C. or lower, the absolute humidity of the object atmosphere becomes zero, which makes it impossible to perform the clogging determination processing based on the humidity of the object atmosphere.

Notably, the VT obtained in S302 may be the latest value or the VTHm or VTLn obtained in S206 or S230.

Next, in S306, the CPU obtains the humidity Hq calculated in S216 or S240. In S308, the CPU determines whether or not a predetermined time (in the present example, 5 seconds) has elapsed. In the case where the result of the determination in S308 is Yes, the CPU proceeds to S310. In the case where the result of the determination in S308 is No, the CPU returns to S306. Namely, the CPU obtains a plurality of values of the humidity Hq within a predetermined time (in the present example, 5 seconds).

Next, in S310, the CPU calculates an average Have(r) from the plurality of values of the humidity Hq obtained within the predetermined time (in the present example, 5 seconds). Notably, r is a natural number which increases chronologically. For example, when Have1(r=1) is obtained by the processing in S310 and the result of the determination in S314 becomes NO, Have2(r=2) is obtained by the processing in S310. The value of r increases by one every time the average is calculated, until the value of r reach 4.

Also, in the present example, since the humidity Hq is obtained each time the time period TW (=200 msec) elapses, 25 values of the humidity Hq are obtained within 5 seconds and are averaged so as to obtain the average Have(r).

Next, in S312, the CPU determines whether or not a predetermined time (in the present example, 55 seconds) has elapsed. In the case where the result of the determination in S312 is Yes, the CPU proceeds to S314. In the case where the result of the determination in S312 is No, the CPU returns to S312. In this manner, in S312, the CPU waits for the predetermined time (in the present example, 55 seconds).

Next, in S314, the CPU determines whether or not the value of r is 4. In the case where the result of the determination in S314 is Yes, the CPU proceeds to S316. In the case where the result of the determination in S314 is No, the CPU returns to S302. In this manner, the CPU calculates four values of Have; i.e., repeats the calculation until Have4 is obtained.

Next, in S316, the CPU obtains the maximum value Have(MAX) and the minimum value Have(MIN) among the four values of Have. Further, in S318, the CPU calculates a difference ΔHave in accordance with the following equation (20).

$$\Delta Have = Have(MAX) - Have(MIN) \quad (20)$$

In S320, the CPU determines whether or not the difference ΔHave is equal to or smaller than a first threshold (in the present example, 0.3 vol % (absolute humidity)). In the case where the result of the determination in S320 is Yes, the CPU determines in S326 that the gas inlet opening 92*h* is "not clogged." Meanwhile, in the case where the result of the determination in S320 is No, the CPU determines in S322 that the gas inlet opening 92*h* is "clogged" and performs processing of sounding an alarm in S324. After that, the CPU ends the subroutine.

As described above, in the first embodiment, the humidity H of the object atmosphere is calculated from the low-temperature-time voltage VL and the high-temperature-time voltage VH which can be measured by the gas detection element 3, and the degree of clogging of the gas inlet opening 92*h* is determined based on a change in the humidity H with time. Therefore, it is unnecessary to newly dispose in the combustible gas detection apparatus 1 a member such as an air flow monitor for determining, through measurement, whether or not clogging has occurred. Therefore, the degree of clogging of the gas inlet opening can be readily determined without increasing the number of components. In the case where a determination is made that the gas inlet opening is clogged, the fact that the detection of gas has become inaccurate or has become impossible can be reported to a user by, for example, sounding an alarm.

Also, in the first embodiment, four humidity data sets Have1 to Have4 are obtained immediately after the startup, after elapse of one minute, after elapse of two minutes, and after elapses of three minutes, respectively, and a change in the humidity is obtained from these data sets. However, the timing of obtaining the humidity data is not limited thereto. Humidity data sets may be obtained at arbitrary timings which are not immediately after the startup, and a change in the humidity may be obtained from the data sets. For example, a gas which differs in humidity from the atmosphere may be jetted to the gas inlet opening at arbitrary timings which are not immediately after the startup, and a change in humidity at that time may be obtained.

Notably, in the first embodiment, the determination as to whether or not the time-course change in the humidity is equal to or smaller than the first threshold is made based on the magnitude relation between the first threshold and ΔHave which is the difference between the maximum value Have(MAX) and the minimum value Have(MIN) among the values of Have. However, the determination method is not limited thereto. For example, the determination may be made by obtaining the inclination of a line representing the time-course change in the humidity from the four values of Have and comparing the inclination with an inclination set as the first threshold.

Also, the processing performed after the determination in S322 that the introduction opening is "clogged" is not limited to the sounding of an alarm in S324. For example, the combustible gas detection apparatus 1 may be forcedly stopped (key off) or a message indicating "clogged" may be displayed on a predetermined display section (for example, a meter or the like of a vehicle).

Clogging Determination Processing According to Second Embodiment

Figure 10:
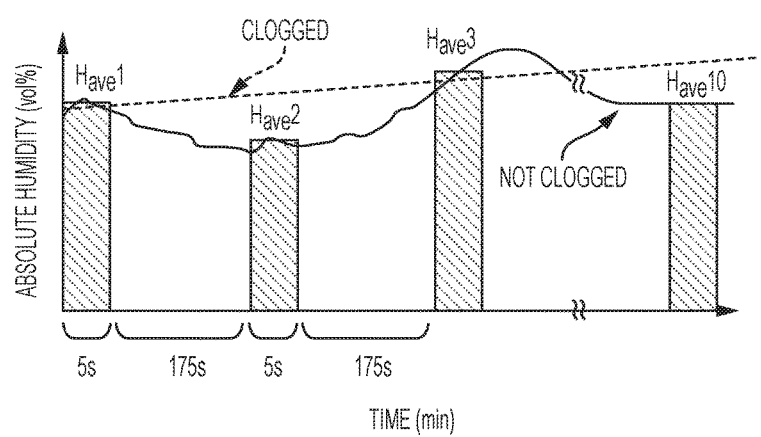
FIG. 10 is a diagram relating to a second embodiment, and showing the concept of clogging determination processing.
Figure 11:
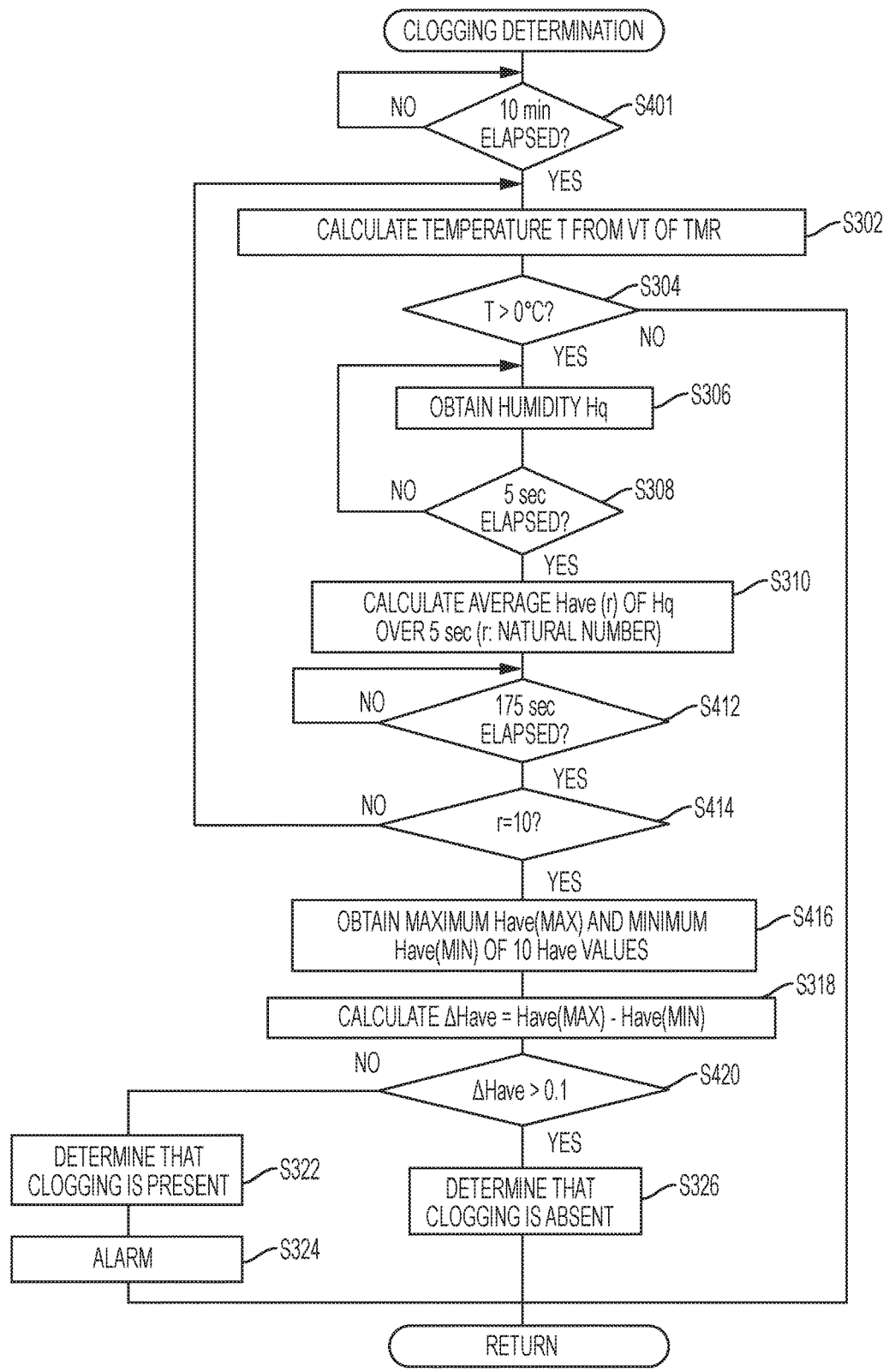
FIG. 11 is a flowchart relating to the second embodiment, and showing the clogging determination processing.
Figure 12A:
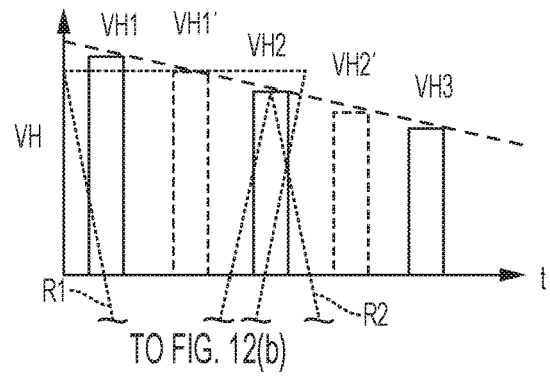
FIGS. 12($a$) and 12($b$) are diagrams representing time charts showing timings at which VH and VL are obtained, FIG. 12($c$) is a diagram representing a time chart showing the first set temperature (CH) and the second set temperature (CL) of the heat generation resistor, and FIG. 12($d$) is a diagram representing a time chart showing timings at which the temperature of the temperature measurement resistor is obtained, in the case where an average high-temperature-time voltage VH' and an average low-temperature-time voltage VL' are used.
Figure 12B:
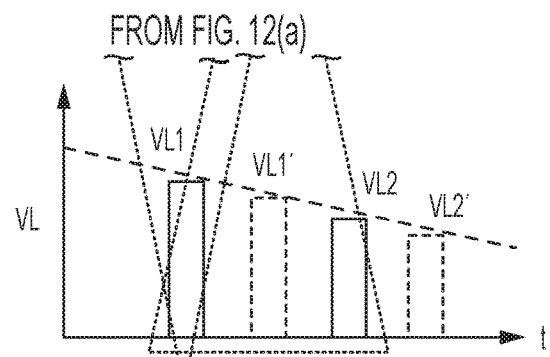
Figure 12C:
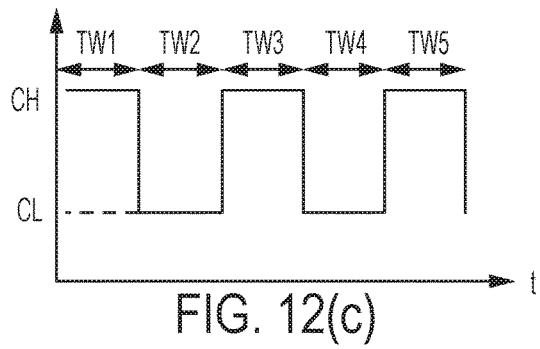
Figure 12D:
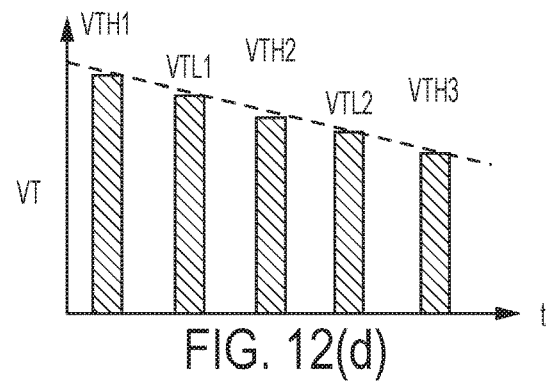

Next, the clogging determination processing of the combustion gas detection apparatus according to a second embodiment of the present invention will be described with reference to FIGS. 10 and 11. Notably, since the gas concentration computation processing and the humidity computation processing are the same as those of the first embodiment, their description is omitted. FIG. 10 is a diagram showing the concept of the clogging determination processing. FIG. 11 is a flowchart showing the clogging determination processing.

FIG. 10 shows an actually measured time-course change in the absolute humidity within the combustible gas detection apparatus 1 after elapse of a predetermined time (in the present example, 10 minutes) after the startup (key on) of the combustible gas detection apparatus for the case where the gas inlet opening 92*h* of the combustible gas detection apparatus 1 was intentionally clogged and the case where the gas inlet opening 92*h* was not clogged.

In the case where the gas inlet opening 92*h* was "not clogged," the absolute humidity within the combustible gas detection apparatus 1 changed with time. Conceivably, this reflects a change in the humidity of the outside air flowing through the gas inlet opening 92*h*. Meanwhile, in the case where the gas inlet opening 92*h* was "clogged," the humidity hardly changed. Conceivably, this phenomenon occurred because the outside air did not flow into the apparatus 1.

Notably, as shown in FIG. 8, when the combustible gas detection apparatus 1 is started, in general, the temperature of the object atmosphere within the combustible gas detection apparatus 1 rises within a short period of time (for example, within 5 minutes) after the startup, and reaches a certain temperature within about 10 minutes. Accordingly, in the second embodiment, the time-course change in the humidity is measured in a period which is after elapse of 10 minutes after the startup and within which the temperature of the object atmosphere within the apparatus 1 is constant.

Namely, it is possible to determine whether or not the gas inlet opening is clogged by determining whether or not the time-course change in the humidity after elapse of a predetermined time (in the present example, 10 minutes) after the startup (key on) of the combustible gas detection apparatus exceeds a second threshold (in the present example, 0.1 vol % (absolute humidity)).

Notably, as shown in FIG. 10, in the second embodiment, ten humidity data sets Have1 to Have10 are obtained at intervals of 3 minutes, and the time-course change is obtained from the ten humidity data sets.

Next, the clogging determination processing based on the concept of FIG. 10 will be described with reference to FIG. 11.

Notably, the processing steps identical with those of the processing flow of FIG. 9 are denoted by the same step numbers, and their description is omitted.

First, in S401, the CPU determines whether or not a predetermined time (in the present example, 10 minutes) has elapsed after the startup (key on) of the combustible gas detection apparatus 1. In the case where the result of the determination in S401 is Yes, the CPU proceeds to S302. In the case where the result of the determination in S401 is No, the CPU waits. This is because, as described above, the temperature of the object atmosphere within the combustible gas detection apparatus 1 becomes constant after elapse of about 10 minutes after the startup.

Subsequently, after the processing of S302 to S310, instead of performing the processing of S312, the CPU performs the processing of S412 so as to determine whether or not a predetermined time (in the present example, 175 seconds) has elapsed. In the case where the result of the determination in S412 is Yes, the CPU proceeds to S414. In the case where the result of the determination in S412 is No, the CPU returns to S412 and waits until 175 seconds has elapsed. Next, instead of performing the processing of S314, the CPU performs the processing of S414 so as to determine whether or not the value of r is 10. In the case where the result of the determination in S414 is Yes, the CPU proceeds to S416. In the case where the result of the determination in S414 is No, the CPU returns to S302. In this manner, the CPU calculates 10 values of Have; i.e., repeats the calculation until Have10 is obtained.

Next, instead of performing the processing of S316, the CPU performs the processing of S416 so as to obtain the maximum value Have(MAX) and the minimum value Have (MIN) among the 10 values of Have. Further, in S318, the CPU calculates a difference ΔHave in accordance with the following equation (20).

$$\Delta Have = Have(MAX) - Have(MIN) \qquad (20)$$

In S420, the CPU determines whether or not the difference ΔHave has exceeded a threshold (in the present example, 0.1). In the case where the result of the determination in S420 is Yes, the CPU determines in S326 that the gas inlet opening 92h is "not clogged" and ends the subroutine. Meanwhile, in the case where the result of the determination in S420 is No, the CPU determines in S322 that the gas inlet opening 92h is "clogged" and performs processing of sounding an alarm in S324. After that, the CPU ends the subroutine.

Notably, in the second embodiment, the determination as to whether or not the time-course change in the humidity is greater than the second threshold is made based on the magnitude relation between the second threshold and ΔHave which is the difference between the maximum value Have (MAX) and the minimum value Have(MIN) among the values of Have. However, the method of determination is not limited thereto. For example, the determination may be made by obtaining the inclination of a line representing the time-course change in the humidity from two successive values of Have and comparing the inclination with an inclination set as the second threshold.

Computation of Humidity H from Average High Temperature Time Voltage or Average Low Temperature Time Voltage Incidentally, in the above-described embodiments, the timing of detection of VH and the timing of detection of VL deviate from each other by an amount corresponding to the time period TW. Therefore, in the case where the environmental temperature changes greatly within a period of time approximately equal to the time period TW, due to the deviation of the detection timings, the calculation accuracy of the ratio between VH and VL; i.e., the humidity H and the gas concentration, may deteriorate.

In order to overcome this drawback, the technique disclosed in Patent Document 2 may be employed. Specifically, by using the average high-temperature-time voltage or average low-temperature-time voltage, the detection timing of the average high-temperature-time voltage or the average low-temperature-time voltage is rendered virtually coincident with that of the low-temperature-time voltage or the high-temperature-time voltage corresponding thereto, whereby the humidity H is calculated more accurately. The processing by this method will be described with reference to FIGS. 12 to 14.

Figure 13:
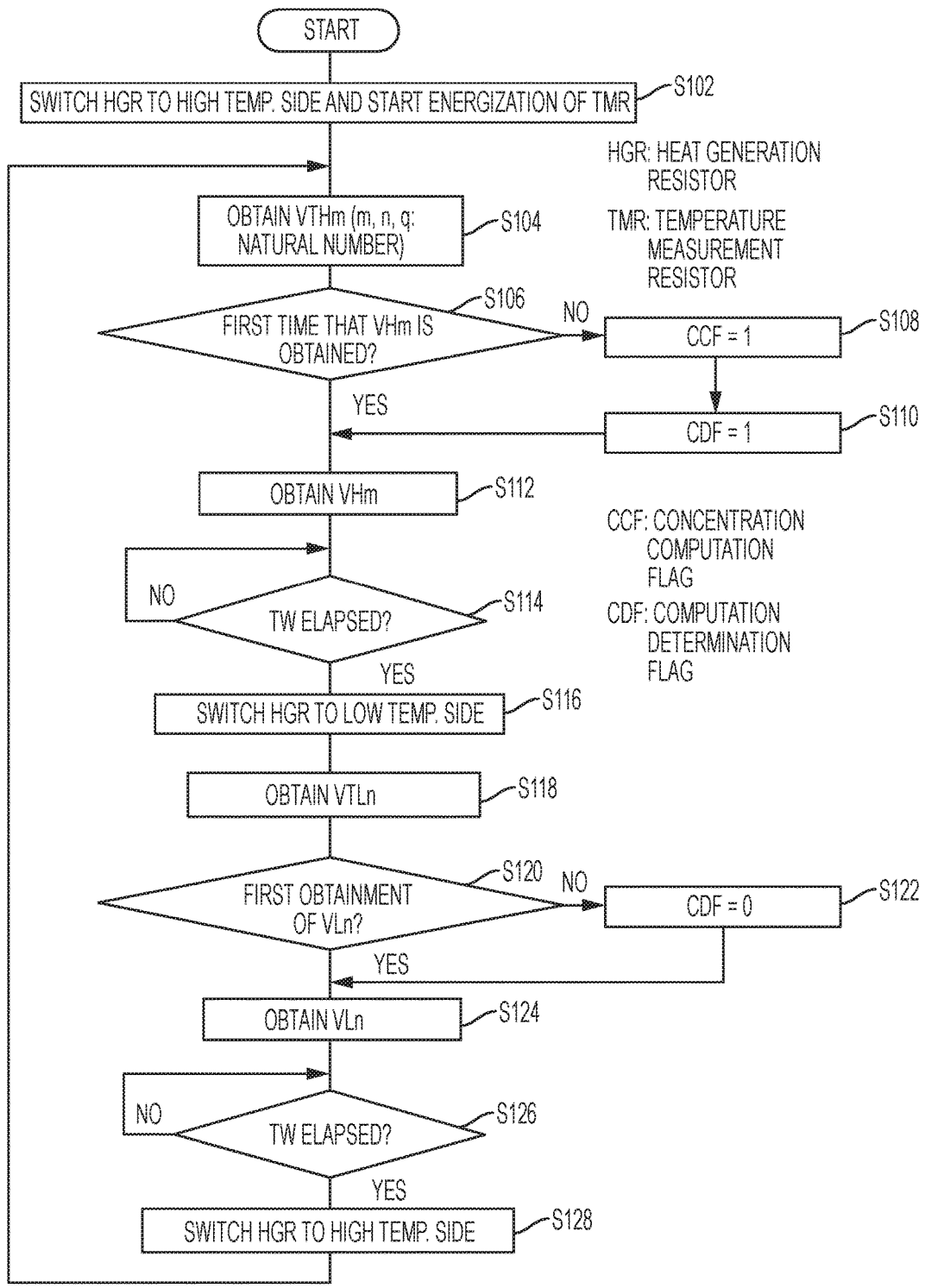
FIG. 13 is a flowchart showing processing of obtaining VH, VL, and VT in the case where the average high-temperature-time voltage VH' and the average low-temperature-time voltage VL' are used.
Figure 14:
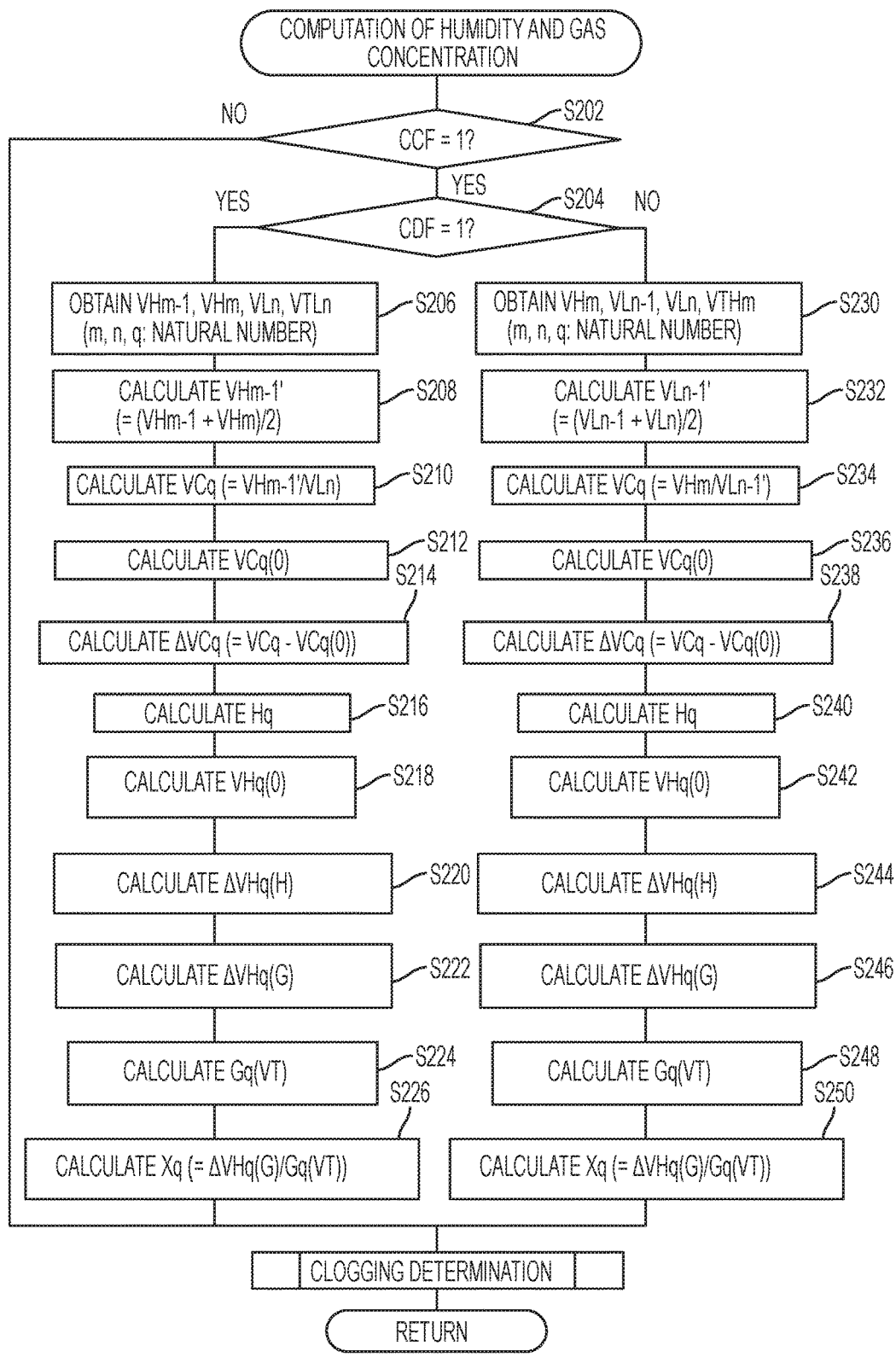
FIG. 14 is a flowchart showing humidity computation processing and gas concentration computation processing performed using the average high-temperature-time voltage VH', and the average low-temperature-time voltage VL'.

FIG. 12 represents time charts (FIGS. 12(*a*) and 12(*b*)) showing timings at which VH and VL are obtained, a time chart (FIG. 12(*c*)) showing the first set temperature (CH) and the second set temperature (CL) of the heat generation resistor, and a time chart (FIG. 12(*d*)) showing timings at which the temperature of the temperature measurement resistor (temperature voltage VT) is obtained. FIG. 13 is a flowchart showing processing of obtaining VH, VL, and VT. FIG. 14 is a flowchart of humidity computation processing and gas concentration computation processing performed using the average high-temperature-time voltage VH' or average low-temperature-time voltage VL'.

First, as shown in FIGS. 12(*a*) and 12(*b*), the CPU computes the humidity and the gas concentration based on the relation (this will be referred to as a "first information group") between an average high-temperature-time voltage VH1' obtained by averaging the two high-temperature-time voltages VH1 and VH2 in time periods TW1 and TW3, which voltages are successive in time, and the low-temperature-time voltage VL1 in a time period TW2 between the time periods TW1 and TW3. The high-temperature-time and low-temperature-time voltages VH and VL used for the first information group are shown in an inverted triangular region R1 in FIG. 12.

As described above, a predictive value of the high-temperature-time voltage (average high-temperature-time voltage VH1') (in time period TW2) at the same detection timing of the low-temperature-time voltage (VL1) is estimated from the high-temperature-time voltages (VH1 and VH2) in other time periods TW1 and TW3. Therefore, the voltage difference and voltage ratio of VH to VL are obtained at the same detection timing, whereby a deterioration in the detection accuracy of humidity caused by a time-course change in the environmental temperature can be suppressed. Also, since the environmental temperature in the time period TW2 (temperature voltage VTL1) is used in the first information group, the environmental temperature whose detection timing is identical with the timing of the calculation of the voltage difference and voltage ratio of VH to VL (first information group) can be used for computing the humidity. Namely, the humidity and gas concentration are computed based on the first information group which is composed of the average high-temperature-time voltage VH1' obtained by averaging the two high-temperature-time voltages VH1 and VH2 which are successive in time, the low-temperature-time voltage VL1 in the time period TW2 between the time periods TW1 and TW3, and the environmental temperature VTL1 in the time period TW2 in which the low-temperature-time voltage VL1 is detected.

Further, after the first information group is calculated in the time period TW3 as described above, an average low-temperature-time voltage VL1' is calculated by averaging the low-temperature-time voltage VL1 used for calculating the first information group and a low-temperature-time voltage VL2 detected in the next time period TW4. Subsequently, the CPU computes the gas concentration based on the relation (this will be referred to as a "second information group") between the average low-temperature-time voltage VL1' and the high-temperature-time voltage VH2 in the time period TW3 between the time periods TW2 and TW4. The high-temperature-time and low-temperature-time voltages VH and VL used for the second information group are shown in a triangular region R2 in FIG. 12.

In the case of the second information group as well, a predictive value of the low-temperature-time voltage (average low-temperature-time voltage VL1') (in time period TW3) at the same detection timing as that of the high-temperature-time voltage (VH2) is estimated from the low-temperature-time voltages (VL1 and VL2) in other time periods TW2 and TW4. Therefore, the voltage difference and voltage ratio of VH to VL are obtained at the same detection timing, whereby a deterioration in detection accuracy of humidity caused by a time-course change in the environmental temperature can be suppressed. Also, since the environmental temperature in the time period TW3 (temperature voltage VTH2) is used in the second information group, the environmental temperature whose detection timing is identical with the timing of the calculation of the voltage difference and voltage ratio of VH to VL (second information group) can be used for computing the humidity. Namely, the humidity and gas concentration are computed based on the second information group which is composed of the average low-temperature-time voltage VL1' obtained by averaging the two low-temperature-time voltages VL1 and VL2 which are successive in time, the high-temperature-time voltage VH2 in the time period TW3 between the time periods TW2 and TW4, and the environmental temperature VTH2 in the time period TW3 in which the high-temperature-time voltage VH2 is detected.

Notably, after the second information group is calculated in the time period TW4 as described above, the CPU calculates the first information group using the high-temperature-time voltage VH2 used for calculating the second information group and a high-temperature-time voltage VH3 detected in the next time period TW5 in the same manner as in the above-described case. As described above, as a result of the first information group and the second information group being calculated alternatingly, the voltage difference and voltage ratio of VH to VL (the first information group and the second information group) are obtained at the same detection timing in each of time periods after the time period TW3; i.e., time periods TW4, TW5, etc. Therefore, the humidity detection accuracy is improved further. In contrast, in the case where only one of the first information group and the second information group is calculated, the intervals between the calculation timing become double the length of the time periods.

Next, the processing of obtaining VH, VL, and VT, the humidity computation processing, and the gas concentration computation processing, which are executed by the CPU of the microcomputer 7, will be described with reference to FIGS. 13 and 14. Notably, in FIGS. 13 and 14, the processing steps identical with those of the processing flows of FIG. FIGS. 6 and 7 are denoted by the same step numbers, and their description is omitted.

As shown in FIG. 13, in S106 subsequent to S102 and S104, the CPU determines whether or not the high-temperature-time voltage (VHm) is being obtained for the first time; i.e., whether or not the high-temperature-time voltage is VH1. In the case where the result of the determination is No, the CPU sets a concentration computation flag to 1 (S108) and sets the computation determination flag to 1 (S110). The CPU then proceeds from S110 to S112. Meanwhile, in the case where the result of the determination in S106 is Yes, the CPU proceeds directly to S112.

Notably, when the concentration computation flag=1, it means that a plurality of high-temperature-time voltages VHm have been obtained and shows that the average high-temperature-time voltage VHm−1' can be obtained by averaging the two successive high-temperature-time voltages VHm−1 and VHm as described in relation to FIG. 12. Notably, the computation determination flag is a flag which is used in the processing shown by the flowchart of FIG. 14 (which will be described below) so as to determine which one of the average high-temperature-time voltage VHm−1' and the average low-temperature-time voltage VLn−1' is to be calculated. In the case where the computation determination flag=1, the CPU performs the processing of calculating the high-temperature-time voltage VHm−1'.

Next, subsequent to S112, the CPU proceeds to S114 through S118 without performing the processing of S113.

Next, in S120, the CPU determines whether or not the low-temperature-time voltage (VLn) is being obtained for the first time; i.e., whether or not the low-temperature-time voltage is VL1. In the case where the result of the determination in S120 is Yes, the CPU proceeds to S124. In the case where the result of the determination in S120 is No, the CPU sets the computation determination flag to 0 (S122). In the case where the computation determination flag=0, the average low-temperature-time voltage VLn−1' can be obtained by averaging the two successive low-temperature-time voltages VLn−1 and VLn as described in relation to FIG. 12. After the processing of S122, the CPU proceeds to S124.

Next, subsequent to S124, the CPU proceeds to S126 through S128 without performing the processing of S125.

The values of VHm, VLn, VTHm, and VTLn obtained as described above are stored in the storage device 8 (RAM) while being related to the concentration computation flag and the computation determination flag, and are read out in the humidity computation processing and the gas concentration computation processing which will be described below.

Next, the humidity computation processing and the gas concentration computation processing will be described with reference to FIG. 14. Notably, since the section of S104 to S114 of FIG. 13 is performed in a certain time period TW, at a point in time after S114, the humidity computation processing and the gas concentration computation processing are performed upon reading the computation determination flag set in S110. Further, the section of S116 to S126 is performed in the next time period TW, and, at a point in time after S126, the next humidity computation processing and the next gas concentration computation processing are performed upon reading the computation determination flag set in S122.

In S202 of FIG. 14, the CPU first determines whether or not the concentration computation flag is 1. In the case where the result of the determination in S202 is Yes, the CPU proceeds to S204. In the case where the result of the determination in S202 is No, the CPU ends the present computation processing and prepares for the next computation processing. Next, in S204, the CPU determines whether or not the computation determination flag is 1. In the case where the result of the determination in S204 is Yes (namely, in the case where two high-temperature-time voltages VHm−1 and VHm which are successive in time have been obtained in S104 through S114 of FIG. 13), the CPU proceeds to S206 and obtains VHm−1, VHm, and VLn from the energization control circuit 50 and VTLn from the temperature adjustment circuit 80. The case where m=2 and n=1 corresponds to the region R1 of FIG. 12, and the CPU performs the processing of computing the gas concentration based on the first information group composed of the average high-temperature-time voltage VHm−1', the low-temperature-time voltage VLn, and the temperature voltage VTLn in the time period in which the low-temperature-time voltage VLn is obtained. Meanwhile, in the case where the result of the determination in S204 is No, the CPU performs the processing of computing the gas concentration based on the second information group composed of the average low-temperature-time voltage VLn−1', the high-temperature-time voltage VHm, and the temperature voltage VTHm in the time period in which the high-temperature-time voltage VHm is obtained.

Next, in S208, the CPU calculates the average high-temperature-time voltage VHm−1'. Specifically, the CPU calculates the average high-temperature-time voltage VHm−1' in accordance with the following equation (1) while using as input values of the equation (1) the VHm−1 and VHm obtained in step S206.

$$VHm-1'=(VHm-1+VHm)/2 \qquad (1)$$

The CPU then proceeds to S210 through S226. In the processing of S210 through S226 of FIG. 14, VHm−1' is used in place of VHm in the processing of S210 through S226 of FIG. 7, and VTLn is used in place of VTHm in the processing of S210 through S226 of FIG. 7.

Meanwhile, in the case where the result of the determination in S204 is No (namely, in the case where two low-temperature-time voltages VLn−1 and VLn which are successive in time have been obtained in S116 through S126 of FIG. 13), the CPU proceeds to S230 and obtains VLn−1, VLn, and VHm from the energization control circuit 50 and VTHm from the temperature adjustment circuit 80. The case where m=2 and n=2 corresponds to the region R2 of FIG. 12.

Next, in S232, the CPU calculates the average low-temperature-time voltage VLn−1'. Specifically, the CPU calculates the average low-temperature-time voltage VLn−1' in accordance with the following equation (6) while using as input values of the equation (6) the VLn−1 and VLn obtained in step S230.

$$VLn-1' = (VLn-1 + VLn)/2 \quad (6)$$

The CPU then proceeds to S234 through S250. In the processing of S234 through S250 of FIG. 14, VHm is used in place of VHm−1 in the processing of S234 through S250 of FIG. 7, VLn−1' is used in place of VLn in the processing of S234 through S250 of FIG. 7, and VTHm is used in place of VTLn in the processing of S234 through S250 of FIG. 7.

The present invention is not limited to the above-described embodiments and encompasses various modifications and equivalents which fall within the spirit and scope of the claims appended hereto.

For example, in the above-described embodiments, a combustible gas detection apparatus is shown as an example. However, the present invention can be applied to a gas detection apparatus for an incombustible gas. Further, the present invention can be applied not only to a gas detection apparatus which computes the gas concentration but also to a gas detection apparatus which functions as a humidity sensor without computing the gas concentration.

In the case where the gas detection apparatus of the present invention calculates the concentration of a gas contained in an object atmosphere, the above-described gas concentration computation section computes the concentration of the gas contained in the object atmosphere using the voltage across the heat generation resistor detected when electric current is supplied to the heat generation resistor by control of the energization control section. Meanwhile, in the case where the gas detection apparatus of the present invention functions as a humidity sensor without computing the concentration of the gas contained in the object atmosphere, the gas detection apparatus does not have the above-described gas concentration computation section, and the humidity computation section computes the humidity as in the above-described embodiment.

The device of the microcomputer 7 which stores various programs and data for executing various processing operations is not limited to the storage device 8 provided in the microcomputer 7, and may be an external storage device or a recording medium which can exchange information with the microcomputer 7. In this case, the microcomputer 7 executes the various processing operations while using the programs and data read out from the external storage device or the recording medium. Examples of the recording medium include a transportable semiconductor memory (e.g., USB memory, memory card (registered trademark), etc.), optical discs such as CD-ROM and DVD, magnetic discs, etc.

Also, the method of computing the gas concentration is not limited to the above-described method.

This application is based on Japanese Patent Application No. 2014-156628 filed Jul. 31, 2014, incorporated herein by reference in its entirety.

What is claimed is:

1. A gas detection apparatus comprising:
a gas detection element which is disposed in an object atmosphere and includes a heat generation resistor whose resistance changes with a change in temperature of the heat generation resistor itself;
an energization control section which switches the energization state of the heat generation resistor when a predetermined period of time has elapsed such that the heat generation resistor alternately assumes one of two resistance values corresponding to one of two set temperatures set in advance; and
a casing member which accommodates the gas detection element and has a gas inlet opening through which the object atmosphere flows between a space inside the casing member and a space outside the casing member,
the gas detection apparatus further comprising:
a humidity computation section which computes the humidity of the object atmosphere based on a ratio of a high-temperature-time voltage to a low-temperature-time voltage, the high-temperature-time voltage being a voltage developed across the heat generation resistor and detected at the high-temperature-side set temperature of the two set temperatures, and the low-temperature-time voltage being a voltage developed across the heat generation resistor and detected at the lower-temperature-side set temperature of the two set temperatures; and
a clogging determination section which determines the degree of clogging of the gas inlet opening based on a change in humidity computed by the humidity computation section.

2. The gas detection apparatus as claimed in claim 1, wherein the clogging determination section determines that the gas inlet opening is clogged in the case where a change in humidity with time exceeds a first threshold within a predetermined period after the gas detection apparatus has been started.

3. The gas detection apparatus as claimed in claim 2, wherein the clogging determination section determines that the gas inlet opening is clogged in the case where a predetermined time has elapsed after the gas detection apparatus has been started and a change in humidity with time does not exceed a second threshold.

4. The gas detection apparatus as claimed in claim 1, wherein the clogging determination section determines that the gas inlet opening is clogged in the case where a predetermined time has elapsed after the gas detection apparatus has been started and a change in humidity with time does not exceed a second threshold.

\* \* \* \* \*